(12) United States Patent
Falconer et al.

(10) Patent No.: US 11,918,974 B2
(45) Date of Patent: Mar. 5, 2024

(54) FUNCTIONALIZATION OF ZEOLITES

(71) Applicant: The Regents of the University of Colorado, Denver, CO (US)

(72) Inventors: John L. Falconer, Boulder, CO (US); James William Medlin, Boulder, CO (US); Lucas Delano Ellis, Boulder, CO (US); Hans H. Funke, Boulder, CO (US); Surya Parker, Jamestown, CO (US)

(73) Assignee: The Regents of the University of Colorado, Denver, CO (US)

( * ) Notice: Subject to any disclaimer, the term of this patent is extended or adjusted under 35 U.S.C. 154(b) by 788 days.

(21) Appl. No.: 16/389,910

(22) Filed: Apr. 19, 2019

(65) Prior Publication Data

US 2019/0329214 A1    Oct. 31, 2019

Related U.S. Application Data

(60) Provisional application No. 62/664,763, filed on Apr. 30, 2018.

(51) Int. Cl.
| | |
|---|---|
| *B01J 20/18* | (2006.01) |
| *B01D 53/02* | (2006.01) |
| *B01J 20/22* | (2006.01) |
| *B01J 20/28* | (2006.01) |

(Continued)

(52) U.S. Cl.
CPC .......... *B01J 20/186* (2013.01); *B01D 53/02* (2013.01); *B01J 20/22* (2013.01); *B01J 20/28016* (2013.01); *B01J 20/3071* (2013.01); *B01J 20/3078* (2013.01); *B01J 20/3085* (2013.01); *C07C 7/13* (2013.01);
(Continued)

(58) Field of Classification Search
CPC ...... B01J 20/186; B01J 20/22; B01J 20/3085; B01J 20/3071; B01J 20/3078; B01J 20/28016; B01D 53/02; B01D 2257/7022; B01D 2253/108; B01D 2256/24
See application file for complete search history.

(56) References Cited

U.S. PATENT DOCUMENTS

| | | | | |
|---|---|---|---|---|
| 5,380,690 | A * | 1/1995 | Zhicheng | B01J 29/40 502/65 |
| 8,475,567 | B2 * | 7/2013 | Cougard | C07C 7/04 95/50 |

(Continued)

OTHER PUBLICATIONS

Cleve et al. (Enhanced hydrothermal stability of -Al2O3 catalyst supports with alkyl phosphonate coatings, Mar. 7, 2018, Langmuir, 34, 3619-3625) (Year: 2018).*

(Continued)

*Primary Examiner* — Youngsul Jeong
(74) *Attorney, Agent, or Firm* — Sheridan Ross P.C.

(57) ABSTRACT

Functionalized zeolites, including a zeolite substrate and a self-assembled monolayer of a phosphonic acid on a surface of the zeolite substrate, are disclosed, as are methods of making and using the functionalized zeolites. The disclosed methods and compositions have various applications, including in the use of molecular sieves to separate small-molecule gases from mixtures thereof. Gas adsorption selectivities and diffusion rates of the functionalized zeolites may be tuned or selected according to the disclosed methods.

6 Claims, 21 Drawing Sheets

(51) Int. Cl.
*B01J 20/30* (2006.01)
*C07C 7/13* (2006.01)

(52) U.S. Cl.
CPC .... *B01D 2253/108* (2013.01); *B01D 2256/24* (2013.01); *B01D 2257/7022* (2013.01)

(56) References Cited

U.S. PATENT DOCUMENTS

| | | | | |
|---|---|---|---|---|
| 10,800,934 | B2* | 10/2020 | Andersen | C04B 35/16 |
| 2013/0281753 | A1* | 10/2013 | McCarthy | B82Y 40/00 |
| | | | | 502/77 |

OTHER PUBLICATIONS

Song et al. (Continuously adjustable, molecular-sieving "Gate" on 5A zeolite for distinguishing small organic molecules by size, 2015, Nature—Scientific Reports, 5:13981 | DOI: 10.1038/srep13981) (Year: 2015).*

Chu et al. (Identifying the effective phosphorous species over modified P-ZSM-5 zeolite: a theoretical study, 2018, Royal Society of Chemistry, vol. 20, pp. 11702-11712) (Year: 2018).*

Ulman (Formation and structure of self-assembled monolayers, Chem. Rev. 1996, 96, 1533-1554, see p. 1534, right column, Section II. Self-Assembled Monolayers) (Year: 1996).*

Bhushan et al., "Applied Scanning Probe Methods IX: Characterization," Springer-Verlag, Berlin, 2008, 436 pages. [Submitted in Four Parts].

Brandt et al., "Chemoselective Catalytic Hydrogenation of Acrolein on Ag(111): Effect of Molecular Orientation on Reaction Selectivity," Journal of the American Chemical Society, vol. 131, No. 47, Nov. 4, 2009, pp. 17286-17290.

Burwell et al., "Modified silica gels as selective adsorbents for sulphur dioxide," Journal of the Chemical Society, Chemical Communications, vol. 342, No. 9, pp. 342-343.

Chandekar et al., "Thermal stability of thiol and silane monolayers: A comparative study," Applied Surface Science, vol. 256, No. 9, Feb. 15, 2010, pp. 2742-2749.

Chudasama et al., "Pore-Size Engineering of Zeolite A for the Size/Shape Selective Molecular Separation," Industrial & Engineering Chemistry Research, vol. 44, No. 6, Feb. 11, 2005, pp. 1780-1786.

Coan et al., "Enhancing Cooperativity in Bifunctional Acid-Pd Catalysts with 2 Carboxylic Acid-Functionalized Organic Monolayers," Journal of Physical Chemistry C, vol. 122, No. 12, 2018, pp. 6637-6647.

Corpuz et al., "Hydrogen Exposure Effects on Pt/Al2O3 Catalysts Coated with Thiolate Monolayers," Langmuir, vol. 30, No. 46, Oct. 29, 2014, pp. 14104-14110.

Ellis et al., "Controlling the Surface Reactivity of Titania via Electronic Tuning of Self-Assembled Monolayers," ACS Catalysis, vol. 7, 2017, pp. 8351-8357.

Gao et al., "Order-Disorder Transitions in Self-Assembled Monolayers: A 13C Solid-State NMR Study," Langmuir, vol. 13, No. 2, Jan. 22, 1997, pp. 115-118.

Gao et al., "Self-Assembled Monolayers of Alkylphosphonic Acids on Metal Oxides," Langmuir, vol. 12, No. 26, Dec. 25, 1996, pp. 6429-6435.

Gawalt et al., "Self-Assembly and Bonding of Alkanephosphonic Acids on the Native Oxide Surface of Titanium," Langmuir, vol. 17, 2001, pp. 5736-5738.

Gobin et al., "Role of the Surface Modification on the Transport of Hexane Isomers in ZSM-5," Journal of Physical Chemistry C, vol. 115, No. 4, Dec. 21, 2010, pp. 1171-1179.

Guerrero et al., "Anchoring of Phosphonate and Phosphinate Coupling Molecules on Titania Particles," Chemistry of Materials, vol. 13, No. 11, Oct. 13, 2001, pp. 4367-4373.

Harlick et al., "Applications of Pore-Expanded Mesoporous Silicas. 3. Triamine Silane Grafting for Enhanced CO2 Adsorption," Industrial & Engineering Chemistry Research, vol. 45, No. 9, Mar. 22, 2006, pp. 3248-3255.

Huang et al., "X-ray powder diffraction analysis of silver behenate, a possible low-angle diffraction standard," Journal of Applied Crystallography, vol. 26, 1993, pp. 180-184.

Huang et al., "Amine-Grafted MCM-48 and Silica Xerogel as Superior Sorbents for Acidic Gas Removal from Natural Gas," Industrial & Engineering Chemistry Research, vol. 42, No. 12, Oct. 26, 2002, pp. 2427-2433.

Javaid et al., "Solubility-based gas separation with oligomer-modified inorganic membranes," Journal of Membrane Science, vol. 187, No. 1-2, Jun. 15, 2001, pp. 141-150.

Kanta et al., "The formation and stability of self-assembled monolayers of octadecylphosphonic acid on titania," Colloids and Surfaces A: Physiochemical and Engineering Aspects, vol. 291, No. 1-3, 2006, pp. 51-58.

Lafond et al., "17O MAS NMR Study of the Bonding Mode of Phosphonate Coupling Molecules in a Titanium Oxo-Alkoxo-Phosphonate and in Titania-Based Hybrid Materials," Chemistry of Materials, vol. 15, No. 21, Sep. 17, 2003, pp. 4098-4103.

Leal et al., "Reversible adsorption of carbon dioxide on amine surface-bonded silica gel," Inorganica Chimica Acta, vol. 240, No. 1-2, Dec. 1995, pp. 183-189.

Li et al., "Effects of impurities on CO2/CH4 separations through SAPO-34 membranes," Journal of Membrane Science, vol. 251, No. 1-2, Apr. 1, 2005, pp. 59-66.

Lien et al., "Control of Pd catalyst selectivity with mixed thiolate monolayers," Journal of Catalysis, vol. 339, Jul. 2016, pp. 38-46.

Luo et al., "Adsorption of CO2, CH4, C3H8, and H2O in SSZ-13, SAPO-34, and T-Type Zeolites," Industrial & Engineering Chemistry Research, vol. 55, No. 35, Aug. 23, 2016, pp. 9749-9757.

Marshall et al., "Adsorption of Oxygenates on Alkanethiol-Functionalized Pd(111) Surfaces: Mechanistic Insights into the Role of Self-Assembled Monolayers on Catalysis," Langmuir, vol. 27, No. 11, Apr. 28, 2011, pp. 6731-6737.

McElwee et al., "Thermal stability of organic monolayers chemically grafted to minerals," Journal of Colloid and Interface Science, vol. 285, No. 2, May 15, 2005, pp. 551-556.

Mutin et al., "Selective Surface Modification of SiO2—TiO2 Supports with Phosphonic Acids," Chemistry of Materials, vol. 16, No. 26, Nov. 17, 2004, pp. 5670-5675.

Negishi et al., "Surface silylation of silicalite membranes and their pervaporation performance for the separation of ethanol from ethanol-water mixtures," Journal of the Ceramic Society of Japan, vol. 122, No. 5, 2014, pp. 357-360.

Niehus et al., "Low-energy ion scattering at surfaces," Surface Science Reports, vol. 17, No. 4-5, May 1993, pp. 213-303.

Pang et al., "Directing reaction pathways by catalyst active-site selection using self-assembled monolayers," Nature Communications, vol. 4, No. 2448, Sep. 12, 2013, 6 pages.

Pawsey et al., "1H Fast MAS NMR Studies of Hydrogen-Bonding Interactions in Self-Assembled Monolayers," Journal of the American Chemical Society, vol. 125, No. 14, Mar. 14, 2003, pp. 4174-4184.

Peralta et al., "Comparison of the Behavior of Metal-Organic Frameworks and Zeolites for Hydrocarbon Separations," Journal of the American Chemical Society, vol. 134, No. 19, Mar. 7, 2012, pp. 8115-8126.

Peter et al., "Selective Adsorption of Oxygen over Argon in Alkaline-Earth-Metal Cation-Exchanged Zeolite X," Industrial & Engineering Chemistry Research, vol. 49, No. 16, Jul. 16, 2010, pp. 7524-7529.

Randon et al., "Modification of ceramic membrane surfaces using phosphoric acid and alkyl phosphonic acids and its effects on ultrafiltration of BSA protein," Journal of Membrane Science, vol. 98, No. 1-2, Jan. 13, 1995, pp. 119-129.

Randon et al., "Preliminary studies on the potential for gas separation by mesoporous ceramic oxide membranes surface modified by alkyl phosphonic acids," Journal of Membrane Science, vol. 134, No. 2, Oct. 29, 1997, pp. 219-223.

(56) References Cited

OTHER PUBLICATIONS

Reitmeier et al., "Enhancement of Sorption Processes in the Zeolite H-ZSM5 by Postsynthetic Surface Modification," Angewandte Chemie International Edition, vol. 48, No. 3, Jan. 5, 2009, pp. 533-538.
Reitmeier et al., "Influence of Postsynthetic Surface Modification on Shape Selective Transport of Aromatic Molecules in HZSM-5," Journal of Physical Chemistry C, vol. 113, No. 34, Jul. 23, 2009, pp. 15355-15363.
Schoenbaum et al., "Controlling the Surface Environment of Heterogeneous Catalysts Using Self-Assembled Monolayers," Accounts of Chemical Research, vol. 47, No. 4, Mar. 17, 2014, pp. 1438-1445.
Sethia et al., "Equilibrium and Dynamic Adsorption of Carbon Monoxide and Nitrogen on ZSM-5 with Different SiO2/Al2O3 Ratio," Separation Science and Technology, vol. 45, No. 3, Feb. 12, 2010, pp. 413-420.
Sholl et al., "Seven chemical separations to change the world," Nature, vol. 532, Apr. 28, 2016, pp. 435-437.
Song et al., "Composite 5A zeolite with ultrathin porous TiO2 coating for selective gas adsorption," Chemical Communications, vol. 52, No. 2, 2015, pp. 373-375.
Song et al., "Continuously Adjustable, Molecular-Sieving "Gate" on 5A Zeolite for Distinguishing Small Organic Molecules by Size," Scientific Reports vol. 5, No. 13981, Sep. 11, 2015, 7 pages.
Song et al., "Molecular Layer Deposition-Modified 5A Zeolite for Highly Efficient CO2 Capture," ACS Applied Materials & Interfaces, vol. 10, No. 1, Dec. 14, 2017, pp. 769-775.
Swain, "chemicalize.org," Journal of Chemical Information and Modeling, vol. 52, No. 2, Feb. 7, 2012, pp. 613.
Van Cleve et al., "Enhanced Hydrothermal Stability of γ-Al2O3 Catalyst Supports with Alkyl Phosphonate Coatings," Langmuir, vol. 34, No. 12, Mar. 7, 2018, pp. 3619-3625.
Vargas-Hernandez et al., "Selective adsorption of ethylene over ethane on natural mordenite and on K+-exchanged mordenite," Adsorption, vol. 21, 2015, pp. 153-163.
Wang et al., "Packing and Thermal Stability of Polyoctadecylsiloxane Compared with Octadecylsilane Monolayers," Langmuir, vol. 16, No. 15, Jun. 23, 2000, pp. 6298-6305.
Watanabe et al., "Multinuclear NMR Studies on the Thermal Stability of SAPO-34," Journal of Catalysis, vol. 143, No. 2, Oct. 1993, pp. 430-436.
Wei et al., "Silane-modified NaA zeolite/PAAS hybrid pervaporation membranes for the dehydration of ethanol," Journal of Applied Polymer Science, vol. 128, No. 5, Jun. 5, 2013, pp. 3390-3397.
Zhang et al., "Control of interfacial acid-metal catalysis with organic monolayers," Nature Catalysis, vol. 1, Jan. 15, 2018, pp. 148-155.
Zhu et al., "Shape selectivity in the adsorption of propane/propene on the all-silica DD3R," Chemical Communications, vol. 24, 1999, pp. 2453-2454.

* cited by examiner

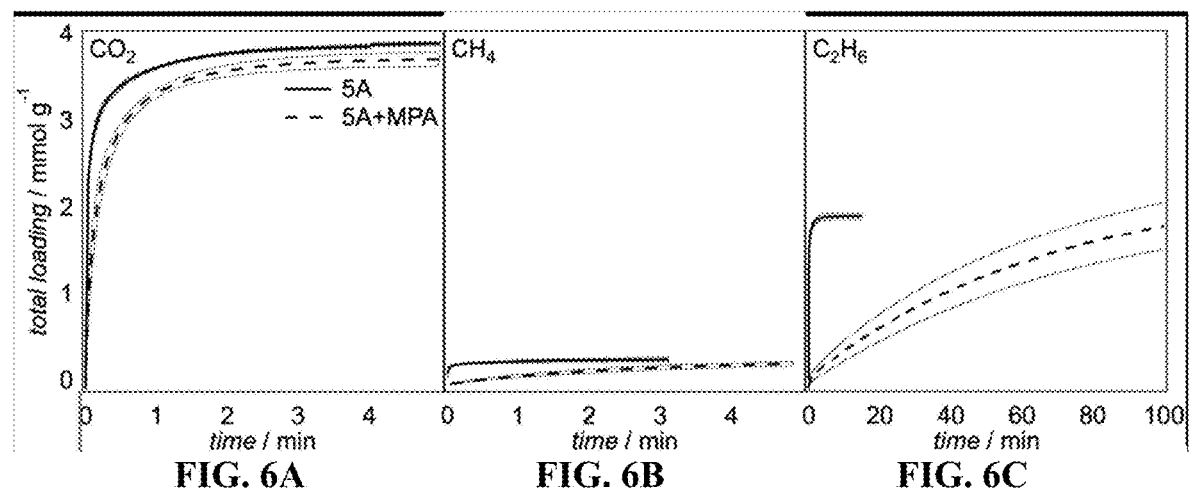
FIG. 6A    FIG. 6B    FIG. 6C
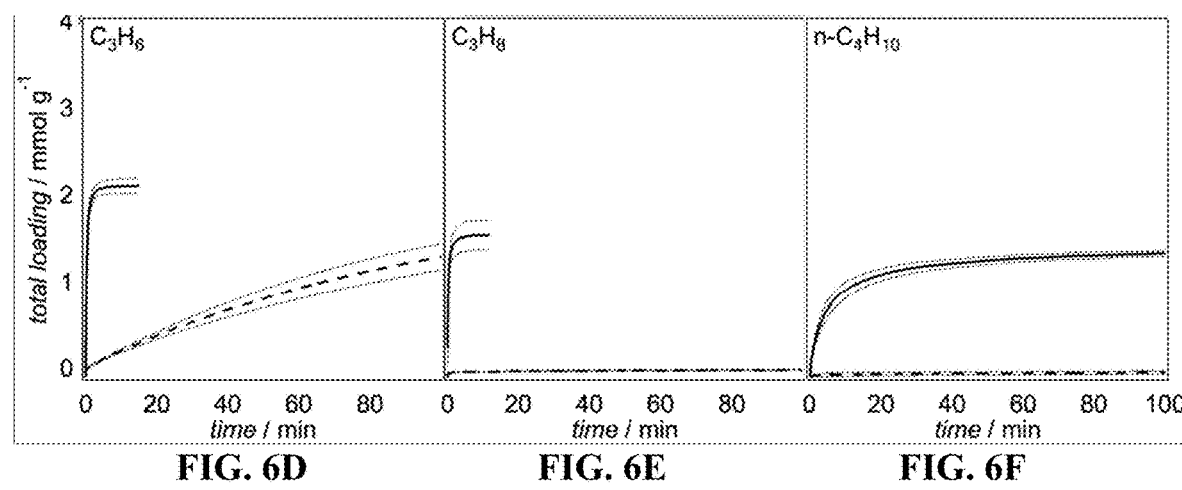
FIG. 6D    FIG. 6E    FIG. 6F

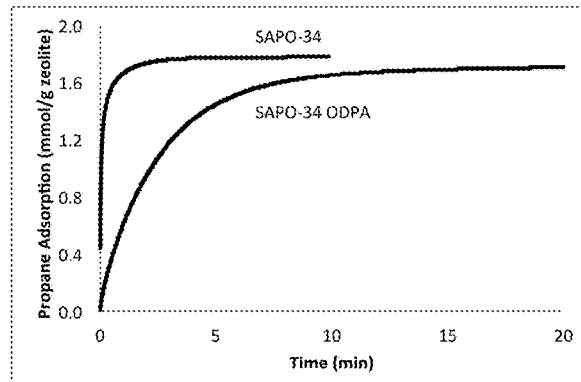 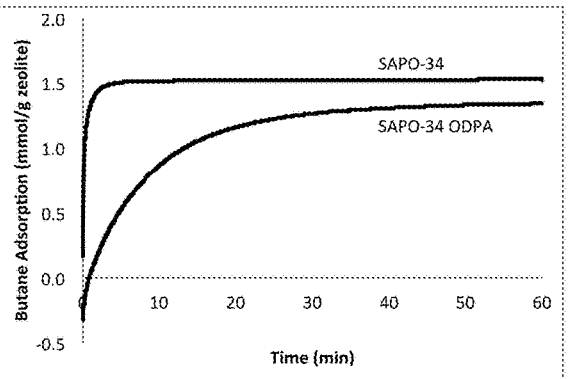
FIG. 15A  FIG. 15B
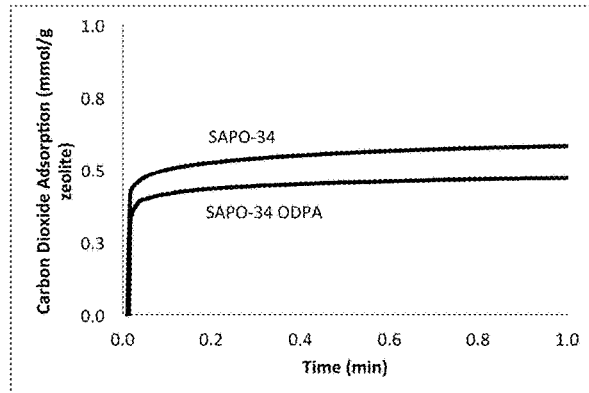 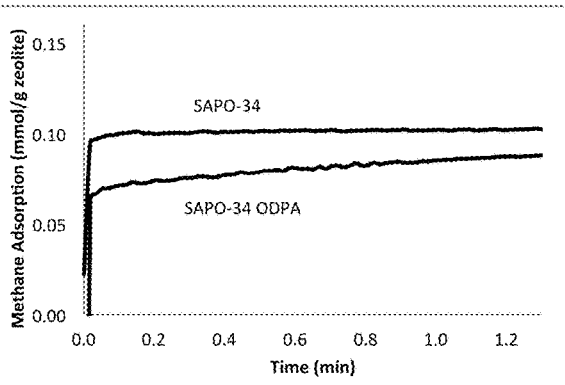
FIG. 15C  FIG. 15D
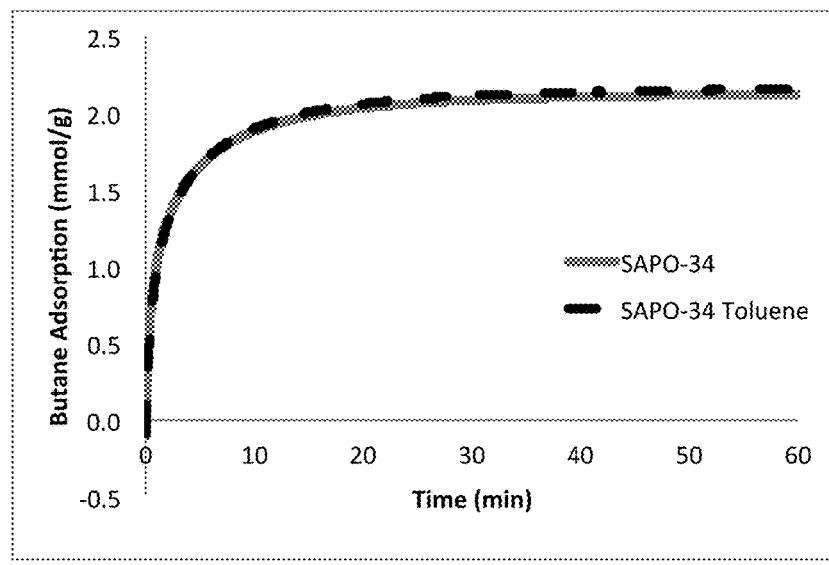
FIG. 16

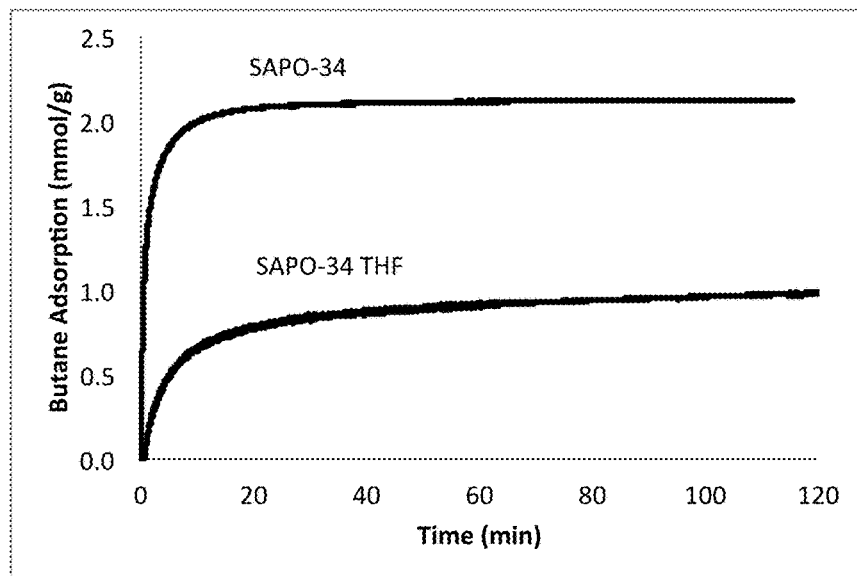
FIG. 29
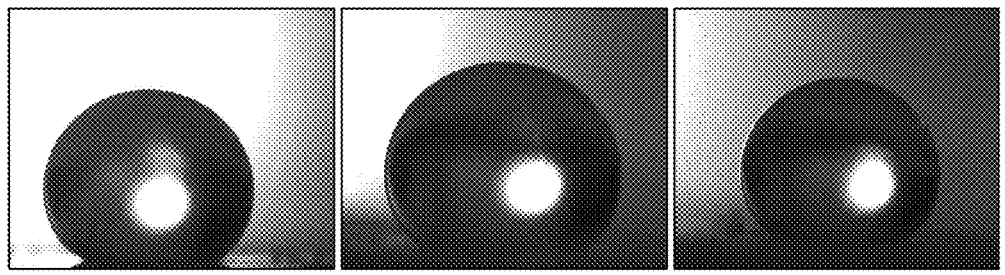
FIG. 30A     FIG. 30B     FIG. 30C
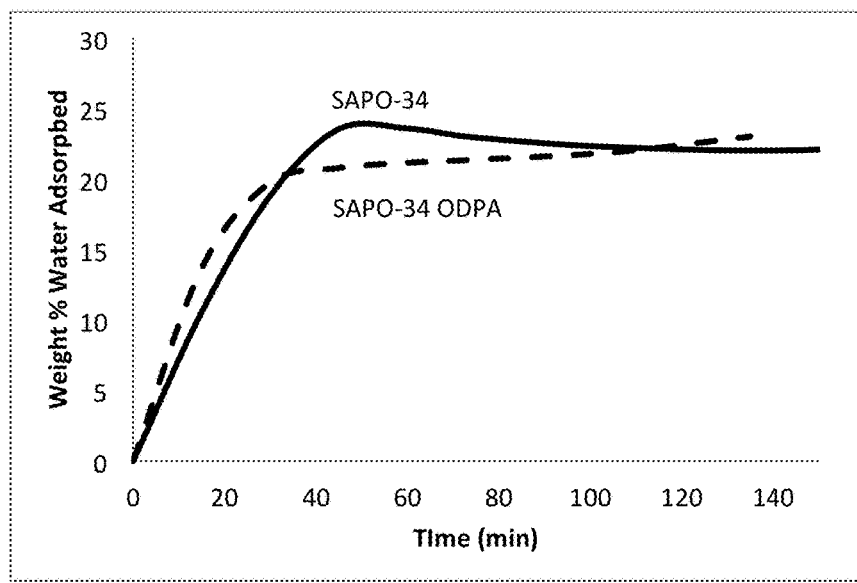
FIG. 31

FUNCTIONALIZATION OF ZEOLITES

CROSS-REFERENCE TO RELATED APPLICATION

This application claims the benefit of U.S. Provisional Patent Application 62/664,763, filed Apr. 30, 2018, the entirety of which is incorporated herein by reference.

FIELD OF THE INVENTION

This invention pertains generally to the functionalization of zeolites, and specifically to the tuning of gas adsorption selectivity and diffusion rates into zeolites by use of phosphonic acid monolayers.

BACKGROUND OF THE INVENTION

The separation of mixtures by distillation to yield high-purity components accounts for 10-15% of the world's energy consumption. Among these separations, alkene/alkane separations are among the most difficult and energy-intensive. For example, propylene ($C_3H_6$) is typically produced via thermal and fluid catalytic cracking of propane ($C_3H_8$), resulting in propylene/propane mixtures; these mixtures are then separated by distillation to obtain polymer-grade propylene, which requires a purity of 99.5%. One estimate suggests that 0.3% of global energy consumption is used to separate propylene and ethylene ($C_2H_4$) from their alkane analogues. More broadly, energy demands are high for many separations of light gases, including ethylene/ethane ($C_2H_6$), ethane/propane/butane ($C_4H_{10}$), and oxygen ($O_2$)/nitrogen ($N_2$) separations. High demand and the energy-intensive nature of conventional separation technologies have spurred significant research efforts into alternative separation technologies, including selective adsorption, amine adsorption (which is economically and energetically inefficient), and the use of membranes.

Application of nanoporous molecular sieves in moving bed or pressure swing adsorption systems has been found to have the potential to significantly decrease energy requirements for propane/propylene separation and other light gas separations. Zeolites have received particular attention as molecular sieves because of their uniform and near-molecular diameter pore sizes. Though zeolites may have a range of pore diameters, commercially available zeolites do not have diameters that are continuous across the range of light gases, and substantial effort has been devoted to creating materials with more tunable pore diameters or chemistries. One approach has been to change the bulk crystal structure or cations within the zeolite; other studies have functionalized the external surface of zeolites with an additional diffusion layer, e.g. by reacting the zeolite with silanes; and hybrid approaches have been used to modify zeolites by functionalizing the pores and external surface with specific functional groups, e.g. amines for binding acids. Recently, zeolite 5A, whose pore diameter of 0.43 nm is close to the molecular diameters of propylene and propane, has been functionalized with titania-based molecular layer deposition (MLD); this increased the propylene/propane ideal adsorption selectivity from 1.2 to 6.0.

One approach that has recently been used to improve the specificity of interactions between organic molecules and porous materials has been in the application of organic self-assembled monolayer (SAM) coatings to heterogeneous catalysts. SAMs are formed using amphiphilic monomers with hydrophilic head groups, which deposit on the substrate surface in solution, and long-chain hydrocarbon tails that align to assemble the monolayer; the self-assembly of the monolayer is spontaneous due to thermodynamically favorable van der Waals interactions between tail groups. Monomer head groups commonly used to form SAMs include silanes, thiols, and phosphonic acids. By tuning the functionality of the organic ligands in SAM coatings, the binding and reaction of organic species on the catalyst can be tuned by effects ranging from steric repulsion to specific non-covalent interactions between the SAM and the reactant.

Because adsorption/desorption is a key phenomenon linking membrane or sorbent separations and catalysis, it has been hypothesized that the application of organic modifiers based on SAM chemistry to zeolites may be applicable to control selectivity in binding for separations; in principle, organic modifiers can alter diffusion characteristics of zeolites through a "gatekeeping" function at the external surface of zeolite particles, or by inducing changes to the pore structure itself. However, self-assembly of monolayers of phosphonic acids—which are particularly desirable head groups due to their high thermal stability—on zeolites has not previously been successful, and the effect of phosphonic acid-based monolayers on zeolites is poorly understood.

There is thus a need in the art for tunable methods and systems for depositing phosphonic acid-based SAMs on zeolites, as well as tuned, functionalized zeolites produced by such methods and systems.

SUMMARY OF THE INVENTION

It is one aspect of the present invention to provide a method for functionalizing a zeolite, comprising (a) providing a zeolite; (b) mixing the zeolite into a solution of a phosphonic acid in a first organic solvent to form a slurry; (c) stirring and centrifuging the slurry and decanting a liquid fraction thereof to form a modified powder; (d) washing or rinsing the modified powder with a second organic solvent; and (e) removing the second organic solvent to obtain the functionalized zeolite.

In embodiments, step (a) may comprise calcining and subsequently cooling a zeolite material.

In embodiments, the zeolite may be selected from the group consisting of zeolite 5A, SAPO-34 zeolite, MFI zeolites, chabazite, Y zeolite, faujasite, ferrierite, mordenite, SSZ-13 zeolite, and ZSM-5 zeolite.

In embodiments, the organic tail of the phosphonic acid may comprise between one and eighteen carbon atoms.

In embodiments, the method may further comprise, between steps (c) and (d), annealing the modified powder.

It is another aspect of the present invention to provide a functionalized zeolite, comprising a zeolite substrate; and a self-assembled monolayer of a phosphonic acid, disposed on a surface of the zeolite substrate.

In embodiments, the zeolite substrate may be annealed.

In embodiments, the zeolite substrate may comprise at least one of a powder and a pellet.

In embodiments, the zeolite substrate may comprise at least one zeolite selected from the group consisting of zeolite 5A, SAPO-34 zeolite, MFI zeolites, chabazite, Y zeolite, faujasite, ferrierite, mordenite, SSZ-13 zeolite, and ZSM-5 zeolite.

In embodiments, the organic tail of the phosphonic acid may comprise between one and eighteen carbon atoms.

In embodiments, the zeolite substrate may comprise zeolite 5A and the phosphonic acid may be methylphosphonic acid.

In embodiments, at least a portion of the monolayer may be disposed on or within a pore of the zeolite substrate.

In embodiments, at least one of the following may be true: (i) the functionalized zeolite has a propylene/propane ideal adsorption selectivity of at least about 45; (ii) the functionalized zeolite has an ethane/propane ideal adsorption selectivity of at least about 44; and (iii) the functionalized zeolite has an ethane/n-butane ideal adsorption selectivity of at least about 13.

In embodiments, an organic tail of the phosphonic acid may comprise at least one of an alkyl chain having between one and eighteen carbon atoms, a branched alkyl group, an unsaturated hydrocarbon including at least one carbon-carbon double (alkene) or triple (alkyne) bond, a haloalkane, a haloarene, an alcohol, an ether, an aldehyde, a ketone, a carboxylic acid, a carboxylate, an ester, an acyl group, an acyl halide, an acid anhydrides, an amine, an amide, a nitrile, an aromatic group, a nonaromatic cyclic group, an organosulfur, an organophosphorus, and an organometallic It is another aspect of the present invention to provide a method for separating a first chemical compound from a mixture comprising the first chemical compound and a second chemical compound, the method comprising contacting the mixture with a functionalized zeolite to selectively sorb the first chemical compound, the functionalized zeolite comprising a zeolite substrate and a self-assembled monolayer of a phosphonic acid disposed on a surface of the zeolite substrate.

In embodiments, at least one of the first chemical compound and the second chemical compound may be selected from the group consisting of carbon dioxide, methane, ethylene, ethane, ethanol, propylene, propane, propanol, butadiene, 1-butene, 2-butene, isobutene, n-butane, isobutane, water, oxygen, and nitrogen.

In embodiments, the first chemical compound may be propane and the second chemical compound may be propylene or vice versa, the zeolite substrate may comprise zeolite 5A, and the phosphonic acid may be methylphosphonic acid.

In embodiments, the functionalized zeolite may have a propylene/propane ideal adsorption selectivity of at least about 45.

In embodiments, the zeolite substrate may comprise at least one zeolite selected from the group consisting of zeolite 5A, SAPO-34 zeolite, MFI zeolites, chabazite, Y zeolite, faujasite, ferrierite, mordenite, SSZ-13 zeolite, and ZSM-5 zeolite.

In embodiments, an organic tail of the phosphonic acid may comprise at least one of an alkyl chain having between one and eighteen carbon atoms, a branched alkyl group, an unsaturated hydrocarbon including at least one carbon-carbon double (alkene) or triple (alkyne) bond, a haloalkane, a haloarene, an alcohol, an ether, an aldehyde, a ketone, a carboxylic acid, a carboxylate, an ester, an acyl group, an acyl halide, an acid anhydrides, an amine, an amide, a nitrile, an aromatic group, a nonaromatic cyclic group, an organosulfur, an organophosphorus, and an organometallic.

While specific embodiments and applications of the present invention have been illustrated and described, it is to be understood that the invention is not limited to the precise configuration and components described herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

The advantages of the present invention will be apparent from the disclosure contained herein.

As used herein, "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B, and C together.

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The embodiments and configurations described herein are neither complete nor exhaustive. As will be appreciated, other embodiments of the invention are possible utilizing, alone or in combination, one or more of the features set forth above or described in detail below.

BRIEF DESCRIPTION OF THE DRAWINGS

FIGS. 6A, 6B, 6C, 6D, 6E, and 6F are pressure decay adsorption profiles of carbon dioxide, methane, ethane, propylene, propane, and n-butane, respectively, in functionalized and unfunctionalized zeolite 5A samples.

FIGS. 15A, 15B, 15C, and 15D are plots of adsorption of propane, n-butane, carbon dioxide, and methane, respectively, on untreated SAPO-34 crystals and SAPO-34 crystals treated with 5 mM $C_{18}$PA in toluene and 4.5 hours of annealing.

FIG. 16 is a plot of n-butane adsorption on SAPO-34, with and without exposure to toluene.

FIG. 29 is a plot of the change in n-butane adsorption on SAPO-34 crystals with and without exposure to THF.

FIGS. 30A, 30B, and 30C are images illustrating water contact angle of SAPO-34 modified with 10 mM $C_{18}$PA in methanol.

FIG. 31 is a plot of water vapor adsorption on SAPO-34 crystals with and without modification by $C_{18}$PA.

DETAILED DESCRIPTION OF THE INVENTION

Figure 1:
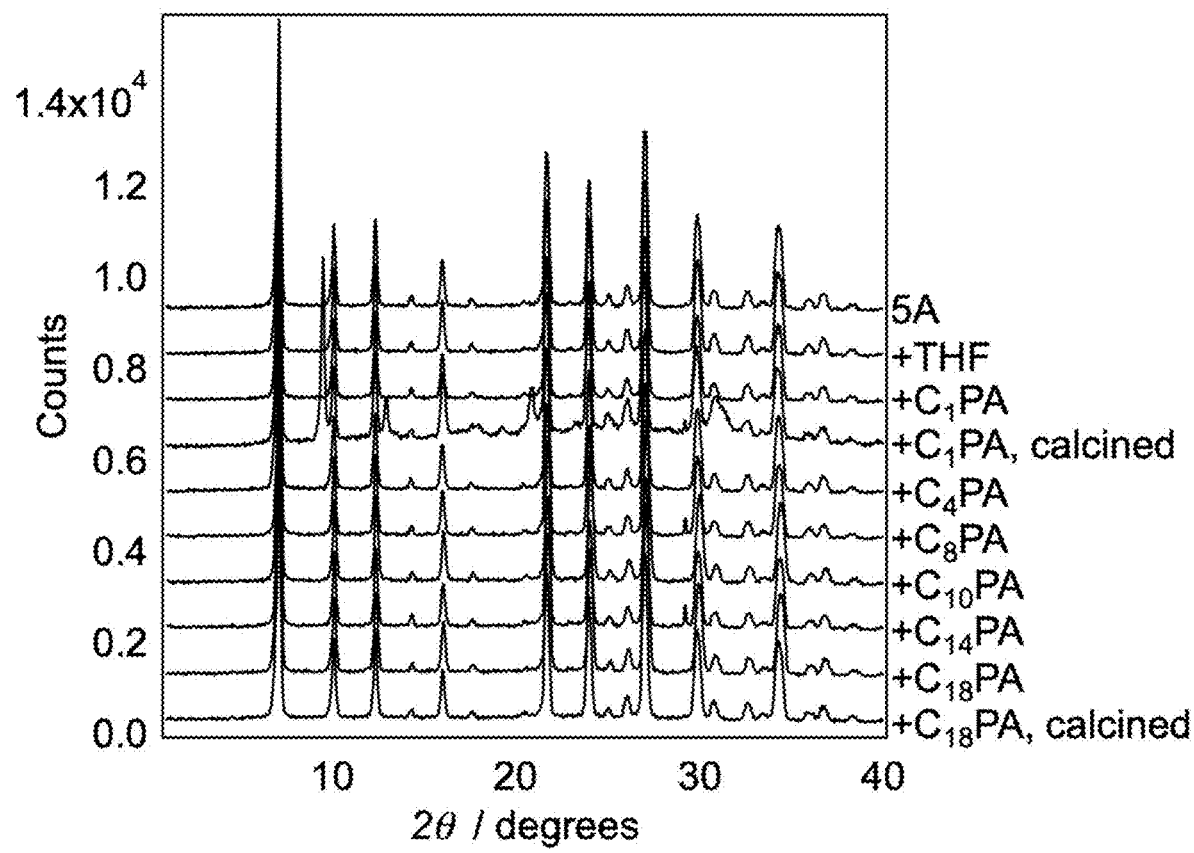
FIG. 1 is a plot of X-ray diffraction of functionalized and unfunctionalized zeolite 5A samples.

As used herein, terms of the form "$C_x$PA" refer to a phosphonic acid (PA) having an organic tail that is x carbon atoms in length, i.e. "$C_1$PA" refers to methylphosphonic acid, "$C_2$PA" refers to ethylphosphonic acid, "$C_3$PA" refers to propylphosphonic acid, "$C_{18}$PA" refers to octadecylphosphonic acid, and so on. $C_1$PA may also be referred to as "MPA," and $C_{18}$PA may also be referred to as "ODPA." Where necessary, a leading letter may indicate a structural isomer of a particular phosphonic acid, e.g. "n$C_4$PA" refers to n-butylphosphonic acid while "t$C_4$PA" refers to tert-butylphosphonic acid, but where no structural isomer leading letter is provided, the linear isomer (n-butyl, n-octadecyl, etc.) may be assumed. It is to be expressly understood that phosphonic acids suitable for use in the present invention may have organic chains or tails other than or in addition to simple linear alkyl hydrocarbon tails, including, by way of non-limiting example, branched alkyl (e.g. tert-butyl) groups, unsaturated hydrocarbons including at least one carbon-carbon double (alkene) or triple (alkyne) bond, haloalkanes and haloarenes, alcohols, ethers, aldehydes, ketones, carboxylic acids, carboxylates, esters, acyl groups, acyl halides, acid anhydrides, amines, amides, nitriles, aromatic and other cyclic groups, and groups including other heteroatoms not previously described (e.g. organosulfur, organophosphorus, and organometallic groups).

As used herein, unless otherwise specified, the term "zeolite" refers to any material having a zeolitic structure, including but not limited to zeolites and zeotypes.

The present inventors have modified zeolites via the deposition of phosphonic acids, and specifically via the deposition of self-assembling monolayers (SAMs) of phosphonic acids. The present inventors have discovered that the size or length of the alkyl tail of the phosphonic acid and other deposition parameters may be utilized as tools to pattern the phosphonic acid on specific locations of the zeolite, allowing the inventors to tune total loadings of certain gases and diffusion rates; this ability results in zeolites capable of efficiently separating molecules of nearly identical size. Without wishing to be bound by any particular theory, it is believed that the size or length of the phosphonic acid tail may govern, at least in part, the extent to which phosphonic acid SAMs penetrate pores of the zeolite, and thus the effective pore size and surface structure of the zeolite may be controlled by choosing a zeolite and a phosphonic acid suitable for a given application. Aspects of the present invention are thus directed to methods and systems for controllably depositing phosphonic acid SAMs on zeolites, and to the tuned, functionalized zeolite compositions themselves. Other aspects of the present invention are directed to methods and systems for separating a mixture of two or more chemical compounds into one or more higher-purity component fractions by utilizing tuned, functionalized zeolites as highly selective molecular sieves. It is to be expressly understood that any zeolite having a pore size and structure suitable for use in a given application may suitably be used in the practice of the present invention, including, by way of non-limiting example, zeolite 5A, SAPO-34 zeolite, WI zeolites, chabazite, Y zeolite, faujasite, ferrierite, mordenite, SSZ-13 zeolite, and ZSM-5 zeolite. Zeolites may also be provided in any suitable physical form, including but not limited to powders and pellets.

The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

Example 1

Characterization of Zeolite 5A Bulk Structure after Phosphonic Acid Modification Zeolite 5A was functionalized by calcining 750 mg of zeolite 5A powder for 4 hours at 400° C., cooling the calcine to room temperature, and then adding the calcine to 180 mL of a 5 mM solution of a phosphonic acid in tetrahydrofuran (THF). For this Example, six phosphonic acids were used: $C_1PA$, n-$C_4PA$, n-$C_8PA$, n-$C_{10}PA$, n-$C_{14}PA$, and n-$C_{18}PA$. The resulting slurry was stirred overnight and centrifuged, and the solvent was then decanted; the resulting powder was annealed in air at 120° C. for 6 hours. The annealed powder was then cooled to room temperature and extensively washed with tetrahydrofuran to remove all physisorbed phosphonic acids. As used in Examples 1-5, unless otherwise noted, the term "native material" refers to zeolite 5A that has been subjected to the process described in this paragraph, except that the liquid to which the calcine was added was pure THF (i.e. did not contain phosphonic acid).

Powder X-ray diffraction (XRD) spectra were obtained with an Inel CPS 120 powder XRD system with a monochromated Cu Kα radiation source that was calibrated with silicon and silver behenate standards, and diffuse reflectance infrared Fourier transform spectroscopy (DRIFTS) was performed using a Harrick Praying Mantis diffuse reflectance accessory (samples were run at atmospheric conditions, using a mirror as a background, with 100 scans at a resolution of 4 cm$^{-1}$).

Figure 2:
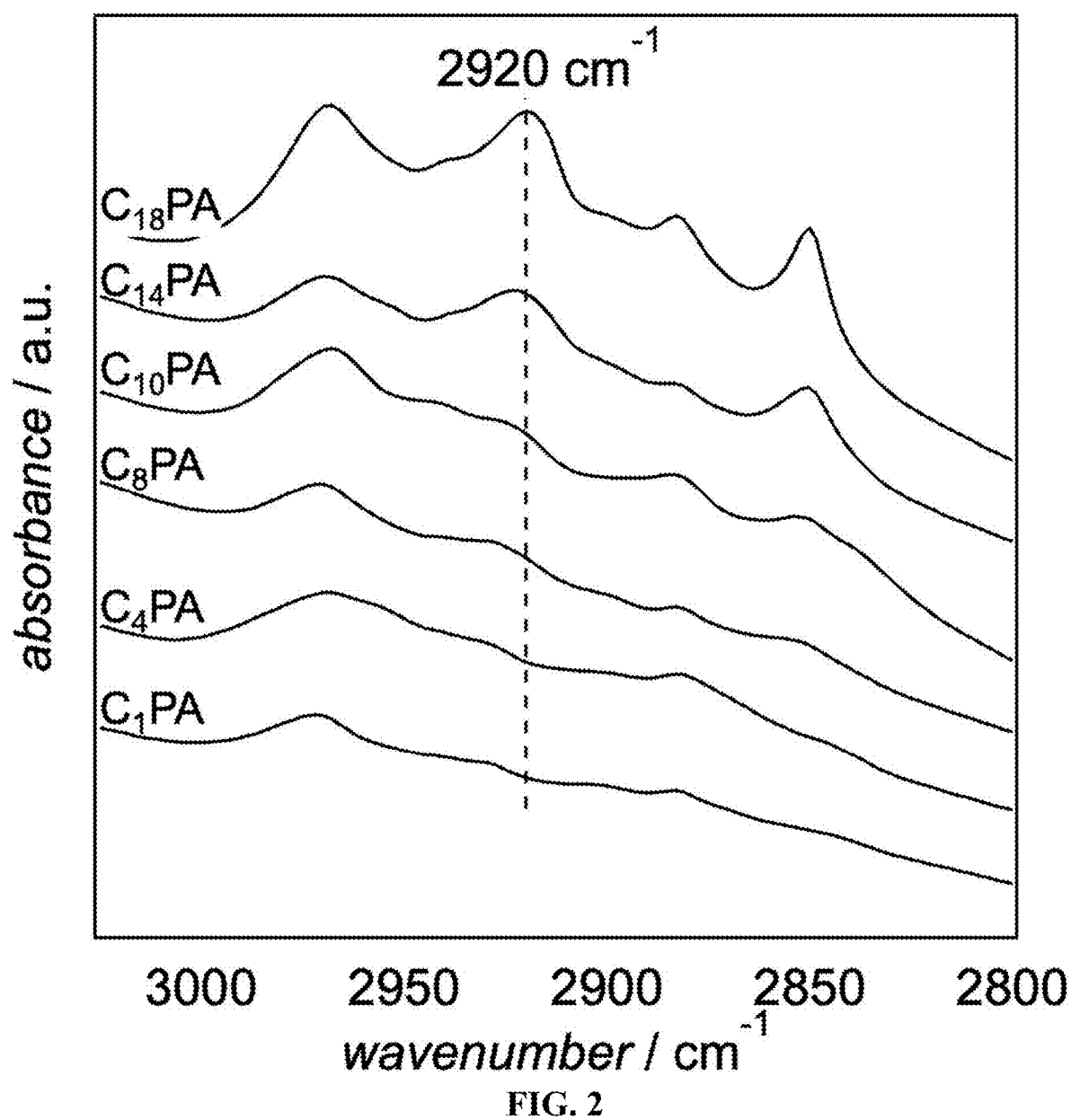
FIG. 2 is a plot of infrared spectroscopy of functionalized zeolite 5A samples.
Figures 3A, 3B, 3C, 3D:
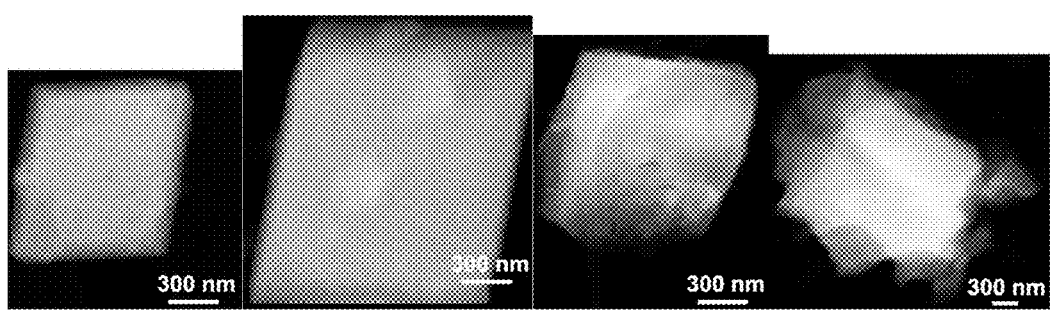
FIG. 3A is a high-angle annular dark field (HAADF) image of a typical octadecylphosphonic acid ($C_{18}PA$)-modified zeolite 5A particle.
FIG. 3B is an HAADF image of a "smooth" methylphosphonic acid ($C_1PA$)-modified zeolite 5A particle.
FIG. 3C is an HAADF image of a "rough" $C_1PA$-modified zeolite 5A particle.
FIG. 3D is an HAADF image of a $C_1PA$-modified zeolite 5A particle calcined at 400° C. for 2 hours.

As indicated by the XRD spectra illustrated by FIG. 1, functionalization of the zeolite did not change the zeolite's bulk crystalline structure, but the presence of the phosphonic acid layer can be confirmed by infrared spectroscopy, as illustrated by FIG. 2. Based on the position of the asymmetric methylene stretch at 2920 cm$^-$ in FIG. 2, the PA coatings having longer alkyl tails (n-$C_{14}PA$ and n-$C_{18}PA$) appear to be relatively well-ordered, similar to monolayers deposited on aluminum oxide, while PA coatings with shorter alkyl tails show blue-shifted stretching frequencies consistent with less ordered films. These trends of ordering with alkyl tail length are consistent with previous studies of organic monolayer-modified catalysts.

Brunauer-Emmett-Teller (BET) surface area measurements were performed on each powder using nitrogen adsorption in triplicates after pretreating samples at 200° C. for 3 hours in an atmosphere of 30% nitrogen ($N_2$) and 70% helium, and phosphorus loadings were measured by inductively coupled plasma mass spectrometry (ICP-MS). The results are presented in Table 1.

TABLE 1

BET surface area and ICP-MS elemental composition of zeolite materials

| Zeolite material | BET surface area (m$^2$/g) | Phosphorus content (wt %) |
|---|---|---|
| Native | 386 ± 20 | Below detection limit |
| $C_1$PA-modified | 316 ± 22 | 0.8 ± 0.26 |
| $C_4$PA-modified | 365 ± 25 | 0.1 ± 0.01 |
| $C_8$PA-modified | 359 ± 20 | 0.1 ± 0.01 |
| $C_{10}$PA-modified | 416 ± 58 | Below detection limit |
| $C_{14}$PA-modified | 394 ± 17 | Below detection limit |
| $C_{18}$PA-modified | 395 ± 12 | Below detection limit |

The BET surface area measurements and elemental analysis presented in Table 1 are consistent with most of the phosphonic acid being deposited on the external surface of the zeolite, with similar surface areas measured for native and functionalized materials. However, zeolites modified with the smallest phosphonic acid, $C_1PA$, had a lower surface area than the native material and much higher levels of phosphorus than any other material. Although $C_1PA$ has been found to form somewhat denser coatings on the surface of other substrates, e.g. aluminum oxide, the increase in phosphorus loading (approximately an order of magnitude relative to other samples) suggests more extensive modification of the zeolite.

Example 2

Effect of Phosphonic Acid Alkyl Tail Length on Extent of Zeolite Modification

Scanning transmission electron microscopy (STEM) images and energy dispersive X-ray spectroscopy (EDS) maps of the $C_1PA$- and $C_{18}PA$-functionalized zeolite powders described in Example 1 were collected on an FEI Talos F200X device operated at 200 kV; sample powders were dispersed onto a carbon film 300 mesh copper grids. Cross-sectioned samples were prepared by microtoming; powdered samples were mixed into epoxy resin and polymerized overnight in a 60° C. oven, then thin (100 to 150 nm) sections were cut with a diamond knife on a Leica UCT Ultramicrotome and picked up onto copper grids for analysis. Quantification of the chemical content of the zeolite materials was averaged across all imaged areas in each sample; the results of the quantification are presented in Table 2.

TABLE 2

Chemical composition of functionalized zeolite materials

| | | Chemical content (wt %/atom %) | | | | |
|---|---|---|---|---|---|---|
| Particle region | Particle type | P | Si | Al | Ca | Na |
| Entire particle | "Smooth" | 0.72 | 36.33 | 35.18 | 21.55 | 6.22 |
| | $C_1$PA | 0.67 | 37.73 | 38.03 | 15.68 | 7.89 |
| | "Rough" | 7.45 | 38.72 | 32.84 | 17.66 | 7.35 |
| | $C_1$PA | 6.97 | 35.79 | 35.24 | 12.76 | 9.25 |
| | $C_1$PA cross-section | 0.07 | 39.93 | 38.20 | 21.48 | 0.33 |
| | | 0.06 | 41.94 | 41.77 | 15.81 | 0.42 |
| | $C_{18}$PA | 0.18 | 36.69 | 35.35 | 21.43 | 6.34 |
| | | 0.17 | 38.05 | 38.17 | 15.58 | 8.04 |
| | $C_{18}$PA cross-section | 0.29 | 38.63 | 37.42 | 21.33 | 2.33 |
| | | 0.28 | 40.41 | 40.74 | 15.64 | 2.94 |
| Surface of particle | "Smooth" | 3.50 | 36.31 | 33.34 | 21.15 | 5.70 |
| | $C_1$PA | 3.30 | 37.83 | 36.16 | 15.45 | 7.25 |
| | "Rough" | 13.54 | 32.97 | 30.34 | 15.83 | 7.32 |
| | $C_1$PA | 13.11 | 34.03 | 32.61 | 11.45 | 9.23 |

TABLE 2-continued

Chemical composition of functionalized zeolite materials

| Particle region | Particle type | P | Si | Al | Ca | Na |
|---|---|---|---|---|---|---|
| | $C_1PA$ | 0.99 | 40.63 | 37.62 | 20.57 | 0.20 |
| | cross-section | 0.94 | 42.62 | 41.07 | 15.12 | 0.26 |
| | $C_{18}PA$ | 0.97 | 36.57 | 35.38 | 19.94 | 6.65 |
| | | 0.91 | 38.26 | 31.97 | 20.48 | 8.38 |
| | $C_{18}PA$ | 0.40 | 42.86 | 36.88 | 19.44 | 0.42 |
| | cross-section | 0.38 | 44.76 | 40.40 | 14.23 | 0.53 |
| Entire particle, less edges and surface | "Smooth" | 0.42 | 36.39 | 35.36 | 21.61 | 6.22 |
| | $C_1PA$ | 0.39 | 37.78 | 38.21 | 15.72 | 7.89 |
| | "Rough" | 7.19 | 34.74 | 32.95 | 17.70 | 7.42 |
| | $C_1PA$ | 6.73 | 35.80 | 35.34 | 12.78 | 9.34 |
| | $C_1PA$ | 0.02 | 39.64 | 38.29 | 21.75 | 0.30 |
| | cross-section | 0.02 | 41.68 | 41.90 | 16.02 | 0.38 |
| | $C_{18}PA$ | 0.08 | 36.66 | 35.33 | 21.62 | 6.31 |
| | | 0.07 | 38.04 | 38.16 | 15.72 | 8.00 |
| | $C_{18}PA$ | 0.02 | 39.00 | 36.88 | 21.53 | 2.57 |
| | cross-section | 0.02 | 40.80 | 40.15 | 15.79 | 3.23 |
| Bulk | "Smooth" | 0.31 | 36.48 | 35.36 | 21.67 | 6.19 |
| | $C_1PA$ | 0.29 | 37.87 | 38.22 | 15.77 | 7.85 |
| | "Rough" | 4.28 | 35.70 | 34.65 | 18.18 | 7.20 |
| | $C_1PA$ | 3.99 | 36.73 | 37.11 | 13.11 | 9.05 |
| | $C_1PA$ | 0.00 | 38.95 | 38.94 | 21.99 | 0.10 |
| | cross-section | 0.00 | 40.99 | 42.66 | 16.22 | 0.13 |
| | $C_{18}PA$ | 0.03 | 36.63 | 35.71 | 21.03 | 6.59 |
| | | 0.03 | 37.91 | 38.47 | 15.26 | 8.32 |
| | $C_{18}PA$ | 0.40 | 42.86 | 36.88 | 19.44 | 0.42 |
| | cross-section | 0.38 | 44.76 | 40.40 | 14.23 | 0.53 |

As illustrated by FIGS. 3A through 3D and the obtained EDS maps (not shown in the Figures), analysis of different regions of the functionalized materials indicates enrichment near the surface of the zeolite in both $C_1PA$- and $C_{18}PA$-modified materials. As in Example 1, concentrations of phosphorus were much higher in the $C_1PA$-modified samples and there was some variation across $C_1PA$-modified crystallites, with the phosphorus content appearing to be much higher on samples with greater surface roughness. Without wishing to be bound by any particular theory, it is believed that $C_1PA$ is more capable than $C_{18}PA$ of binding in high densities near the external surface of the zeolite to more significantly alter the pore entrance region. Localization of phosphorus near the surface is further supported by detailed quantification of different regions of the full zeolite and analysis of cross-section samples of the zeolite, as shown in Table 2; phosphorus content was shown to be lower when the edges of the particles were excluded and much lower in the center of the particle.

To complement these techniques, low-energy ion scattering (LEIS) analysis was carried out by IonTOF on a Qtac100 instrument using a 5 keV $^4He^+$ beam and an analysis current of 2 nanoamperes; to establish peak positions for the elements aluminum, silicon, and phosphorus, aluminum oxide ($Al_2O_3$), silicon dioxide ($SiO_2$), and calcium pyrophosphate ($Ca_2P_2O_7$) were used as reference materials. The LEIS spectra (not shown in the Figures) indicated, for the $C_{18}PA$-coated zeolites, only surface carbon could be detected (no surface phosphorus, silicon, or aluminum was present), which is consistent with extensive modification of the outer zeolite surface with a dense layer of alkyl ligands. For the $C_1PA$-coated zeolite, substantial carbon signal was also detected (not shown), but signals from phosphorus, aluminum, and silicon were prominent as well; as discussed in greater detail below, LEIS experiments following calcination of the samples suggests that phosphorus content was significantly higher in $C_1PA$-coated samples than in $C_{18}PA$-coated samples.

Example 3

Dependence of Gas Permeabilities and Selectivities on Phosphonic Acid Alkyl Tail Length Pressure decay adsorption and isotherm measurements of the functionalized zeolite powders described in Example 1 were performed on an Autosorb-1 instrument equipped with a custom LabVIEW-based data acquisition system. Pressure decay adsorption was performed at a manifold pressure of 100 kPa after samples had been pretreated for 3 hours at 200° C. under vacuum.

Figures 4A, 4B:
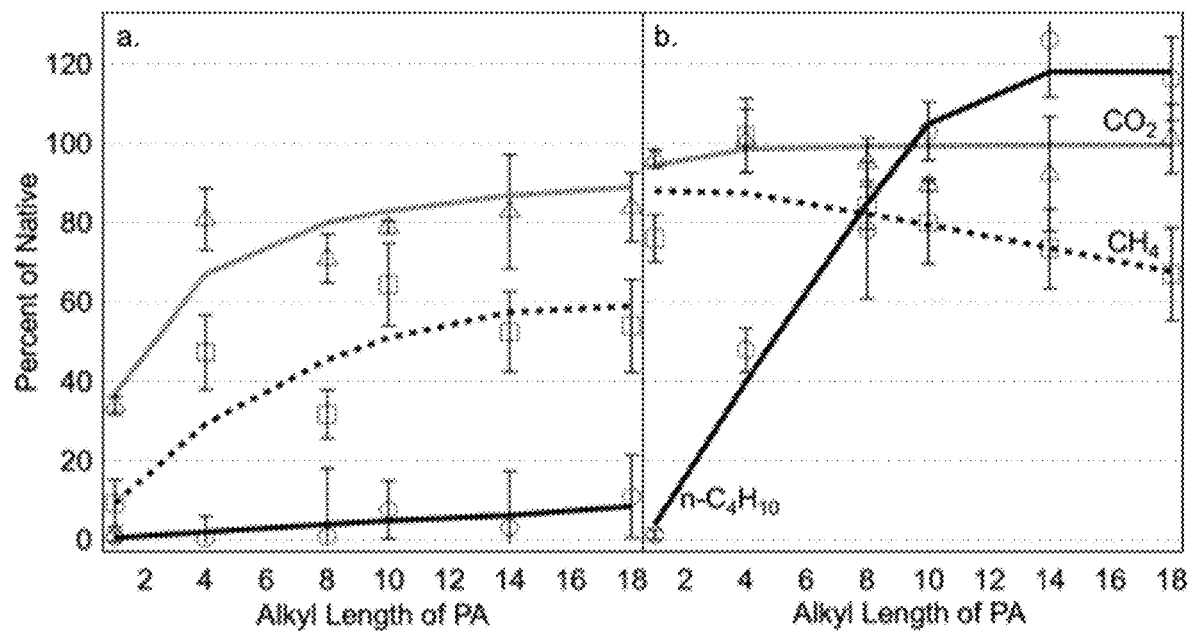
FIG. 4A is a plot of initial diffusion rate of carbon dioxide ($CO_2$, triangles), methane ($CH_4$, squares), and n-butane (circles) as a function of alkyl tail length of the phosphonic acid modifier.
FIG. 4B is a plot of total loading of carbon dioxide (triangles), methane (squares), and n-butane (circles) as a function of alkyl tail length of the phosphonic acid modifier.
Figure 5:
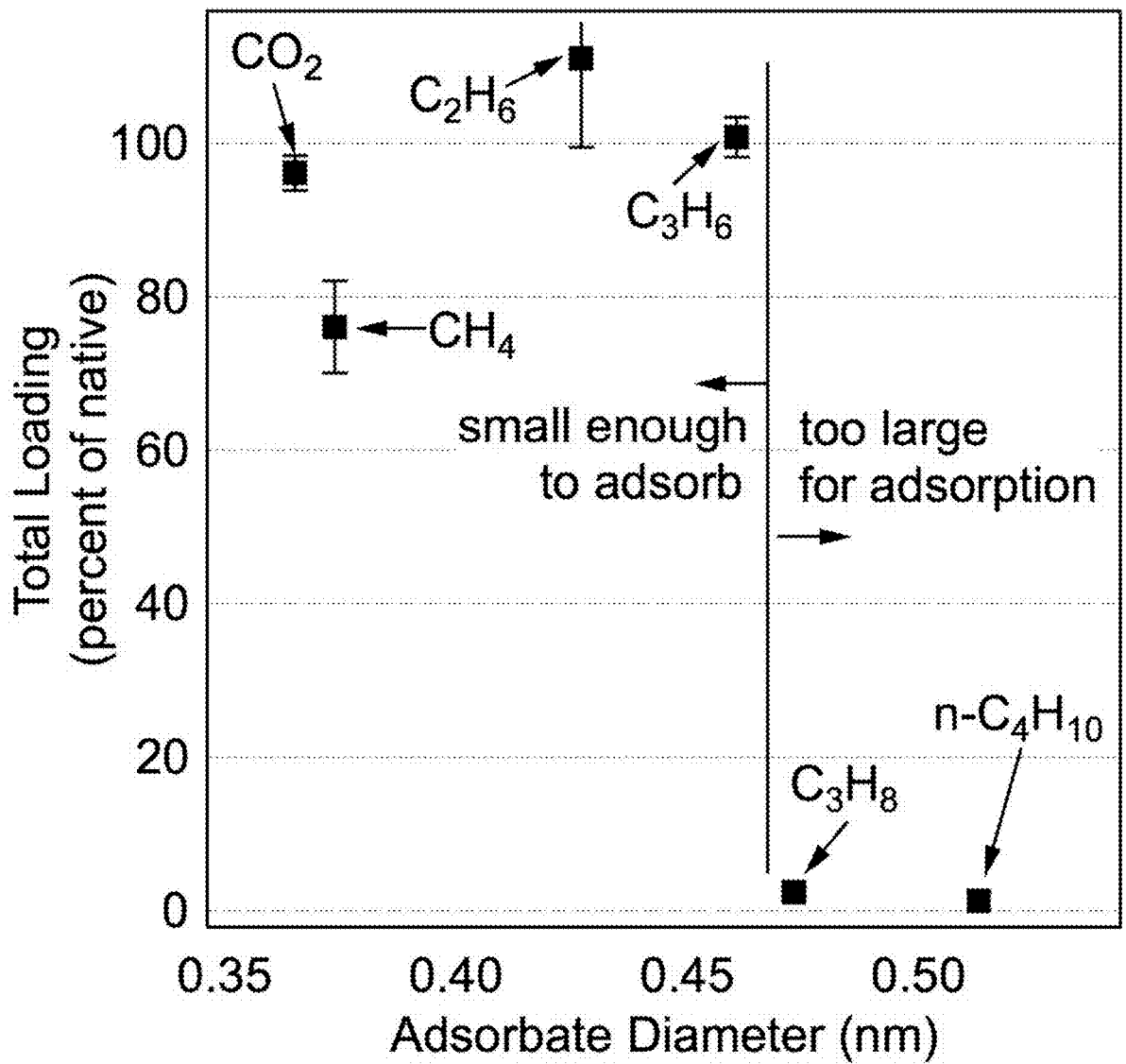
FIG. 5 is a plot of normalized total loading of carbon dioxide, methane, ethane, propylene, propane, and n-butane, as a percentage of native performance, for $C_1PA$-modified zeolite 5A as a function of the Chung diameter of each adsorbate molecule.

As illustrated by FIGS. 4A and 4B, the measured loading of n-butane increased with length of the phosphonic acid alkyl tail from $C_1$ (1.3% of native material) up to $C_{14}$, but the phosphonic acid modifier with the longest alkyl tail, $C_{18}$, had a similar equilibrium n-butane loading as the uncoated zeolite (i.e. native) material. The initial diffusion rate of n-butane is also strongly affected by the phosphonic acid modifiers, although all of the modifiers slowed n-butane diffusion by a large margin; while it is difficult to ascertain a trend in the n-butane diffusion rates, it is notable that the diffusion rate for the $C_1PA$-modified material is just 0.6% that of the native material.

FIGS. 4A and 4B also illustrate that the diffusion rate and equilibrium uptake of molecules smaller than n-butane are much less affected by the phosphonic acid modification. Carbon dioxide and methane equilibrium loadings were similar for all modified zeolites, and all were 70-100% of the loading of the native material. The diffusion rates of both carbon dioxide and methane were similar for all zeolites modified with $C_4PA$ and larger acids, equating to about 80% of the loading of the native material for carbon dioxide and about 50% of the loading of the native material for methane.

The clear outlier to the above-referenced trends was zeolites functionalized with $C_1PA$. The initial diffusion rates of carbon dioxide (34.9% of native) and methane (9.3% of native) were both much lower than the other functionalized materials, but the total achievable loading was roughly identical to that of the native material; by contrast, total loading of n-butane on the $C_1PA$-functionalized zeolite is only about 1% that of the native material.

Figure 7:
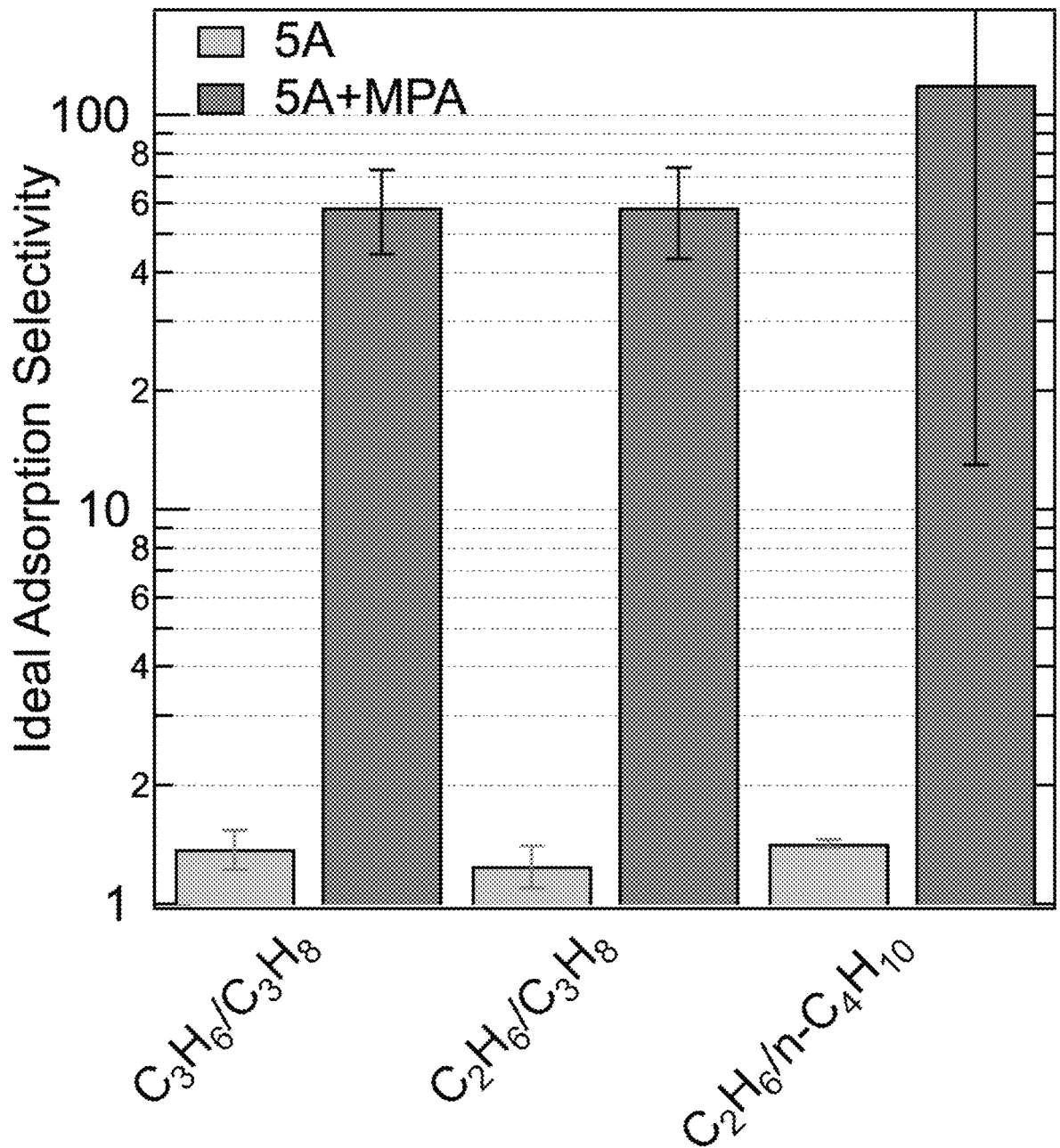
FIG. 7 is a graph of ideal adsorption selectivities in various separations for unmodified zeolite 5A and $C_1PA$-modified zeolite 5A, as calculated from pressure decay adsorption studies at 46 kPa.
Figure 8:
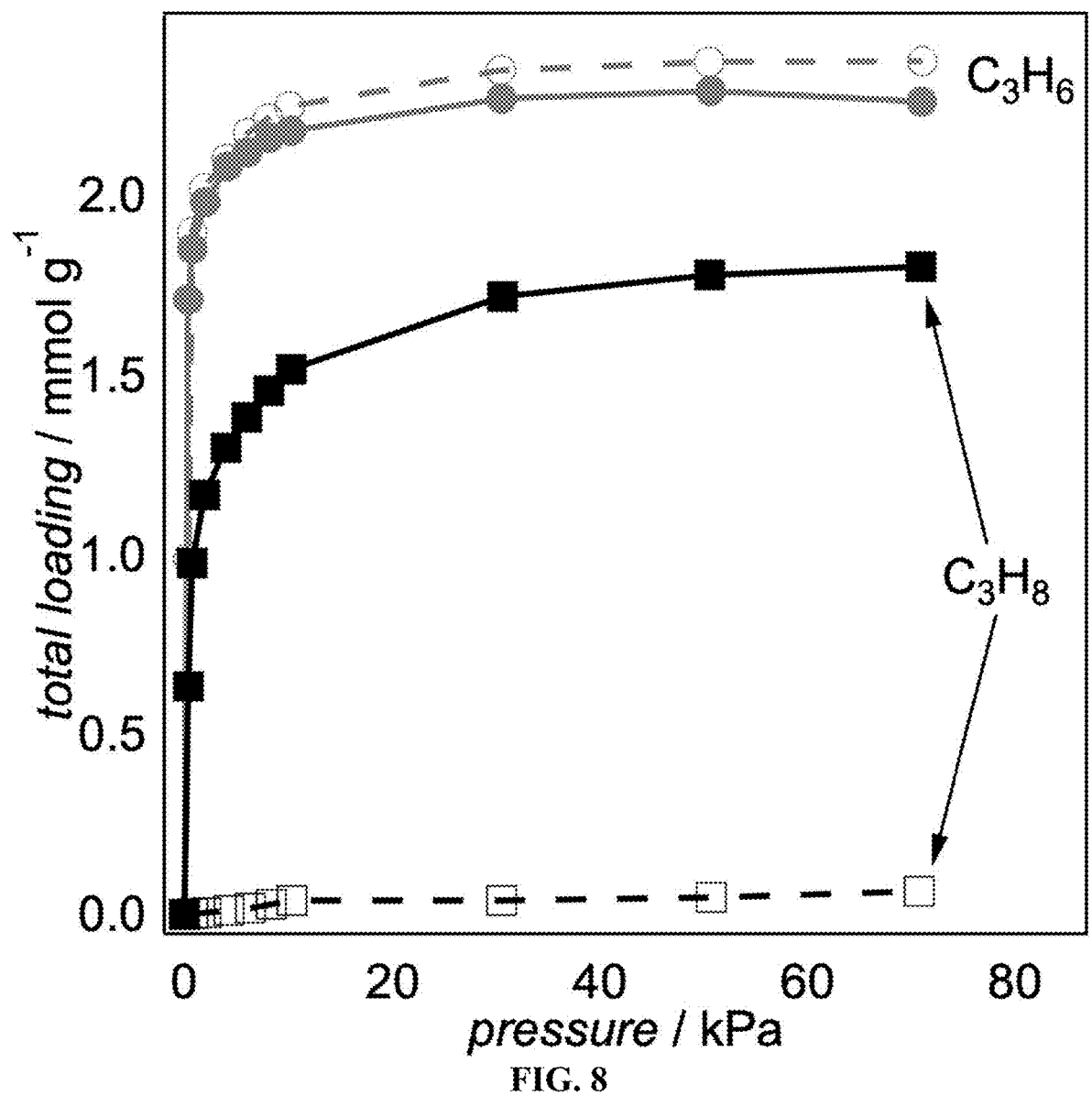
FIG. 8 is a plot of loading isotherms of propane (circles) and propylene (squares) in functionalized and unfunctionalized zeolite 5A samples.

Given the dramatic differences in adsorption performance between the $C_1PA$-modified zeolite and the other modified zeolites, adsorption of ethane, propylene, and propane on the $C_1PA$-modified zeolite was also studied using similar techniques. As illustrated by FIGS. 5 and 6A through 6F, while the loadings of ethane and propylene on the $C_1PA$-modified zeolite did not differ significantly from the native material, the equilibrated propane loading on the $C_1PA$-modified zeolite was only 2.4% of the loading on the native material. As illustrated by FIG. 7, the ideal adsorption selectivity for propylene/propane separation was 1.4±0.2 for the native material, but 59±14 for the $C_1PA$-modified zeolite. Likewise, the ideal adsorption selectivities of the $C_1PA$-modified zeolites for ethane/propane and ethane/n-butane separations were very large (59±15 and 120±107), and much larger than the corresponding selectivities of the native material. Adsorption isotherms for propane and propylene on the $C_1PA$-modified zeolite, illustrated by FIG. 8, show that the ideal propylene/propane adsorption selectivity remains high for this zeolite across a range of pressures.

Figure 9:
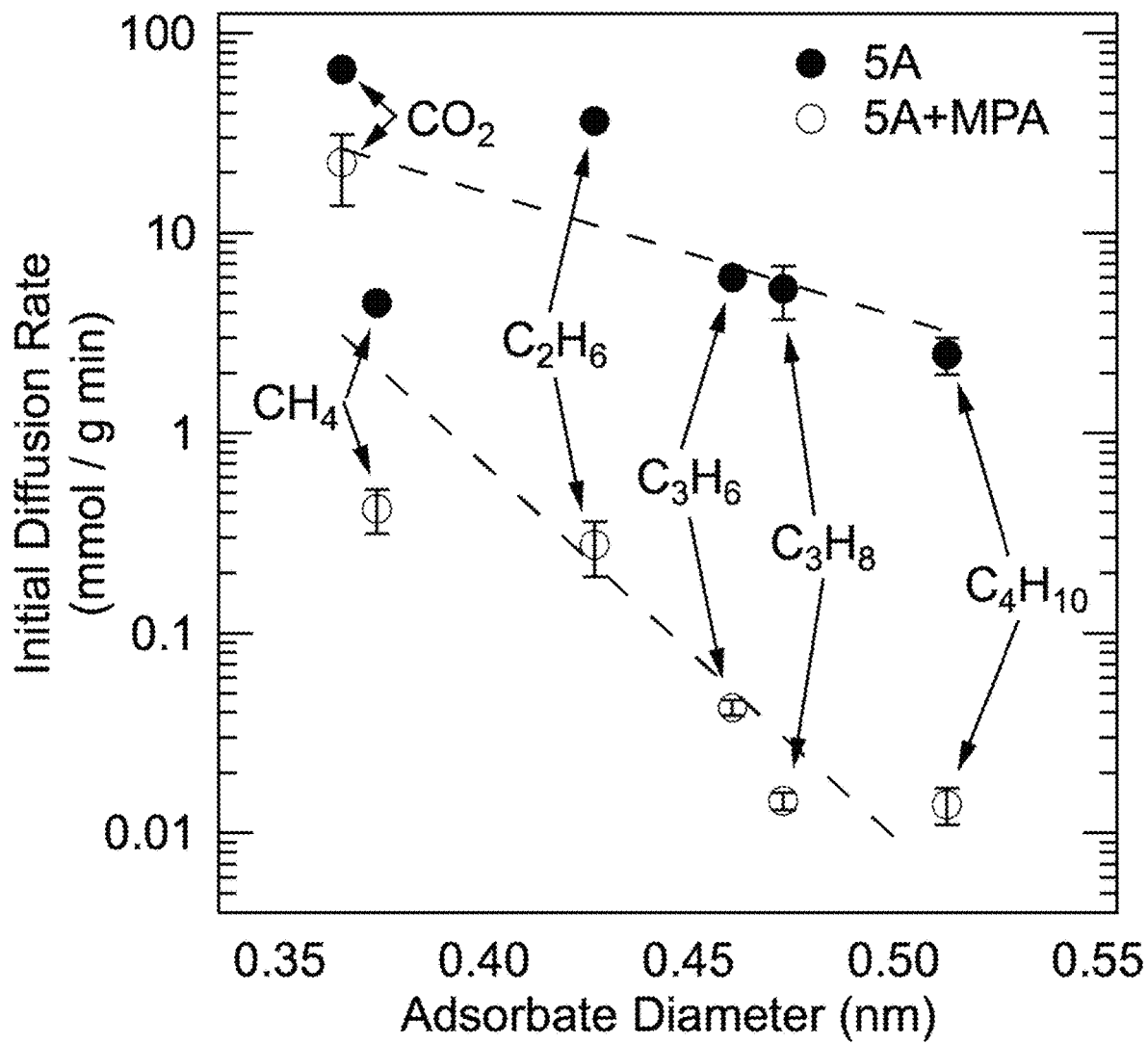
FIG. 9 is a plot of initial diffusion rates of carbon dioxide, methane, ethane, propylene, propane, and n-butane in $C_1PA$-modified zeolite 5A as a function of the Chung diameter of each adsorbate molecule.
Figure 10A:
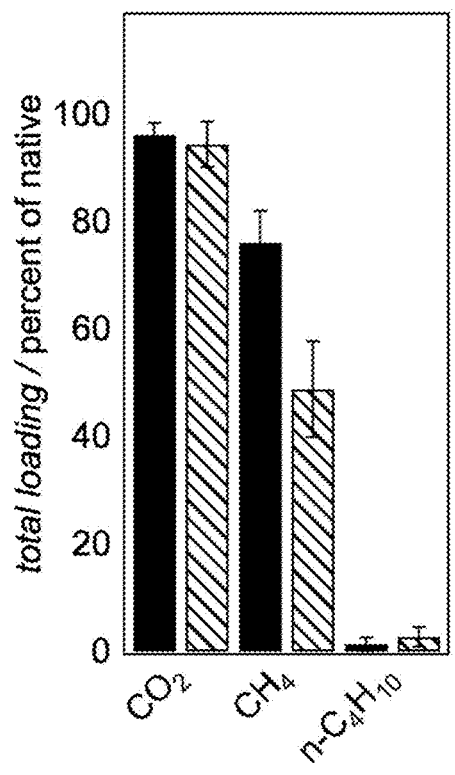
FIGS. 10A and 10B are graphs of total loading and initial diffusion rate, respectively, as a percentage of native for $C_1$PA-modified zeolite 5A particles before and after calcination at 400° C. for 2 hours.
Figure 10B:
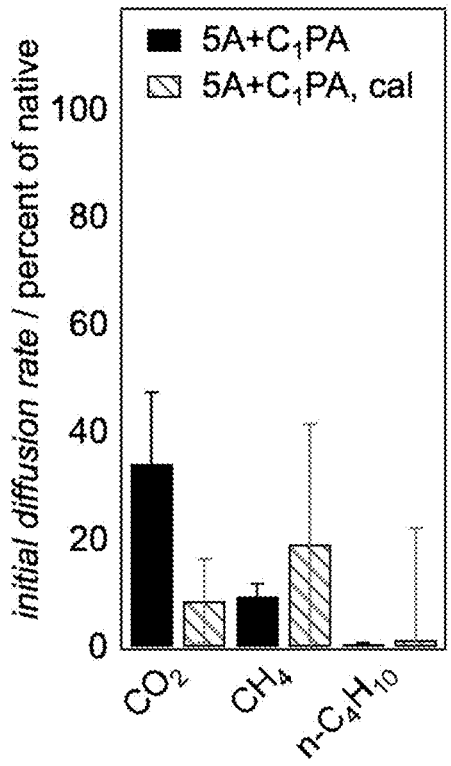
Figure 11A:
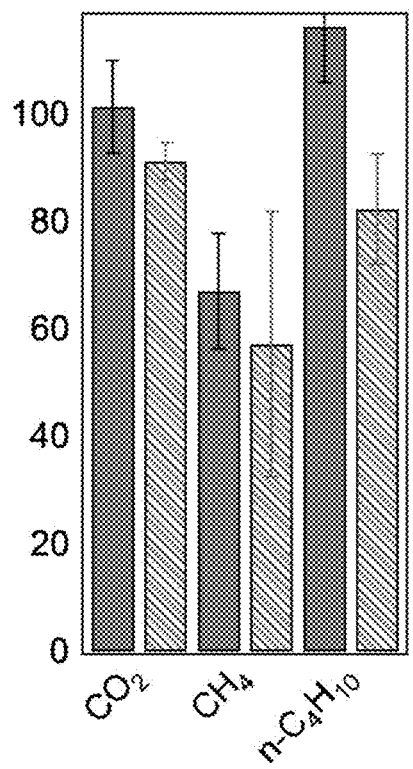
FIGS. 11A and 11B are graphs of total loading and initial diffusion rate, respectively, as a percentage of native for $C_{18}$PA-modified zeolite 5A particles before and after calcination at 400° C. for 2 hours.
Figure 11B:
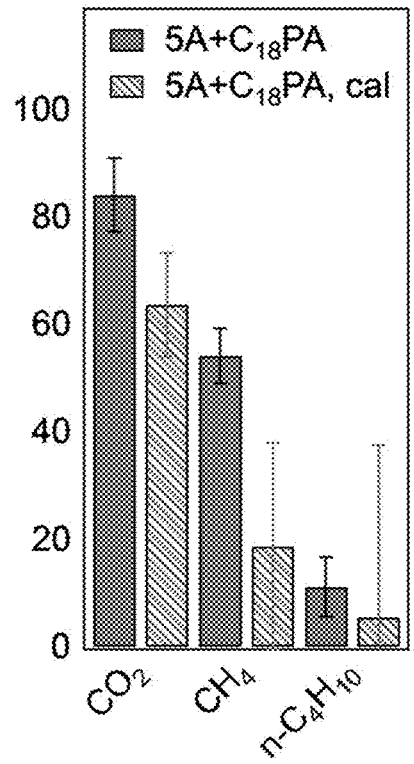
Figures 12A, 12B, 12C, 12D:
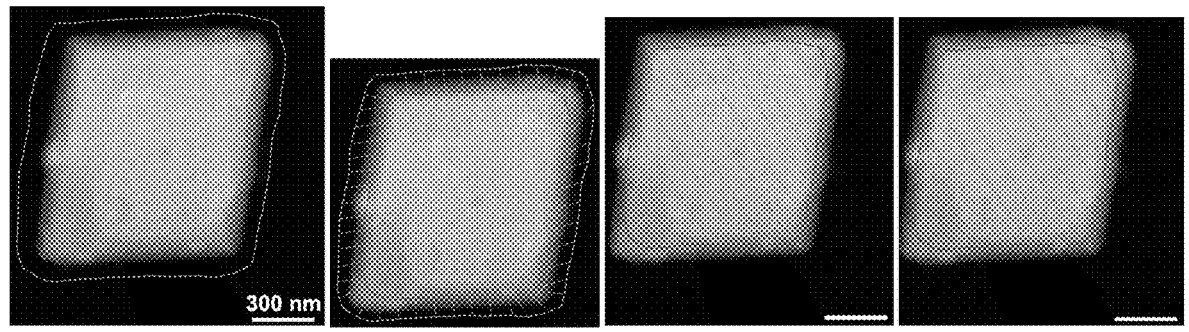
FIGS. 12A, 12B, 12C, and 12D are high-angle dark field images of an entire particle, a surface of a particle, a particle with edges removed, and in bulk, respectively, corresponding to the particle illustrated in FIG. 3A.

Referring now to FIG. 9, the initial diffusion rates of carbon dioxide, methane, ethane, propylene, propane, and n-butane into the native material and the $C_1PA$-functionalized material are illustrated as functions of the Chung diameter. The diffusion rate is more sensitive to adsorbate size in the functionalized zeolite than in the native zeolite: the diffusion rate in the functionalized zeolite is 34% of native for carbon dioxide, but just 1% of native for propylene.

Example 4

Effect of Oxidation of Alkyl Ligands on Zeolite Structure and Gas Permeation Behavior $C_1PA$- and $C_{18}PA$-functionalized zeolites as described in Example 1 were calcined at 400° C. for 2 hours, and the initial diffusion rates and loadings thereon of carbon dioxide, methane, and n-butane were measured according to the procedure of Example 4. The loadings and diffusion rates of the calcined, functionalized zeolites were generally lower for all gases than for their uncalcined counterparts, as illustrated by FIGS. 10A through 11B, but the $C_{18}PA$-functionalized zeolites still adsorbed far more n-butane than did the $C_1PA$-functionalized zeolites. Preliminary STEM and EDS studies indicate that the calcination process results in significant redistribution of phosphorus throughout the zeolite, suggesting diffusion of phosphorus into the bulk (see, e.g., FIGS. 12A through 12D and Table 2). LEIS measurements show that the calcination resulted in substantial, but incomplete, removal of carbon from the surface of the $C_{18}PA$-functionalized zeolites, such that surface phosphorus, silicon, and aluminum could be detected. Changes in peak intensities of the calcined species relative to the uncalcined species in the EDS maps (not shown in the Figures) illustrated that calcination of $C_1PA$-coated samples resulted in a significant (about twofold) decrease in the measured ratio of phosphorus to combined silicon and aluminum, indicating that the calcination was accompanied by reduced surface enrichment of phosphorus. Without wishing to be bound by any particular theory, it is believed that the ligand plays a key role in controlling the location of the phosphonic acid modifiers, confining them to the surface (as in the case of $C_4PA$ and longer-tailed modifiers) or near the surface (as in the case of $C_1PA$ modifiers).

Example 5

Further Spectroscopic and Analytical Characterization of Functionalized Zeolites As Examples 1 through 4 illustrate for zeolite 5A, $C_1PA$ modifiers have a much larger effect on diffusion and adsorption of light gases than phosphonic acids having alkyl ligands containing four or more carbon atoms. Without wishing to be bound by any particular theory, it is believed that these differences result from the smaller molecular size of $C_1PA$ relative to other phosphonic acid modifiers, which allows $C_1PA$ molecules to access sites in the near-surface region (perhaps at the pore entrance) of the zeolite particle; this hypothesis is consistent with the smaller BET surface area, higher surface phosphorus content, and much smaller propane and n-butane uptake for $C_1PA$-modified zeolites than for zeolites modified with other phosphonic acids.

Projected minimum diameters of various SAM and adsorbate molecules were calculated using the online software package Chemicalize™. The results are presented in Table 3.

TABLE 3

Projected minimum diameter of SAM and adsorbate molecules

| Molecule | Projected minimum diameter (nm) |
|---|---|
| $C_1PA$ | 0.62 |
| $C_4PA$ | 0.63 |
| $C_8PA$ | 0.66 |
| $C_{10}PA$ | 0.79 |
| $C_{14}PA$ | 0.89 |
| $C_{18}PA$ | 0.98 |
| Carbon dioxide | 0.43 |
| Methane | 0.42 |
| Ethane | 0.47 |
| Propylene | 0.53 |
| Propane | 0.54 |
| N-butane | 0.54 |

As shown in Table 3, the projected minimum diameter of $C_1PA$ is estimated to be approximately 35% smaller than the projected minimum diameter of $C_{18}PA$. Without wishing to be bound by any particular theory, the observed sensitivity of diffusion to molecular size suggests that $C_1PA$ either partially blocks the zeolite pore entrance or occupies some of the internal volume at positions close to the external surface.

Phosphorus nuclear magnetic resonance (NMR) spectra were collected in a 7 T Bruker Avance IIIHD 300 spectrometer measuring at 121.5 MHz; the spectrometer was calibrated using ammonium dihydrogen phosphate (ADP) set to 0 ppm. Samples were prepared by placing approximately 100 mg of hydrated zeolite into a 4 mm zirconia rotor and spinning at 10 kHz, and spectra were collected with proton decoupling at a frequency of 300.2 MHz. Measurements of the $C_1PA$-modified zeolite were made using a 1-microsecond pulse with a 5-second delay between pulses over a total of 256 scans, and measurements of the $C_{18}PA$-modified zeolite were made using a 1-microsecond pulse with a 1-second delay between pulses over a total of 1,280 scans.

Figure 13A:
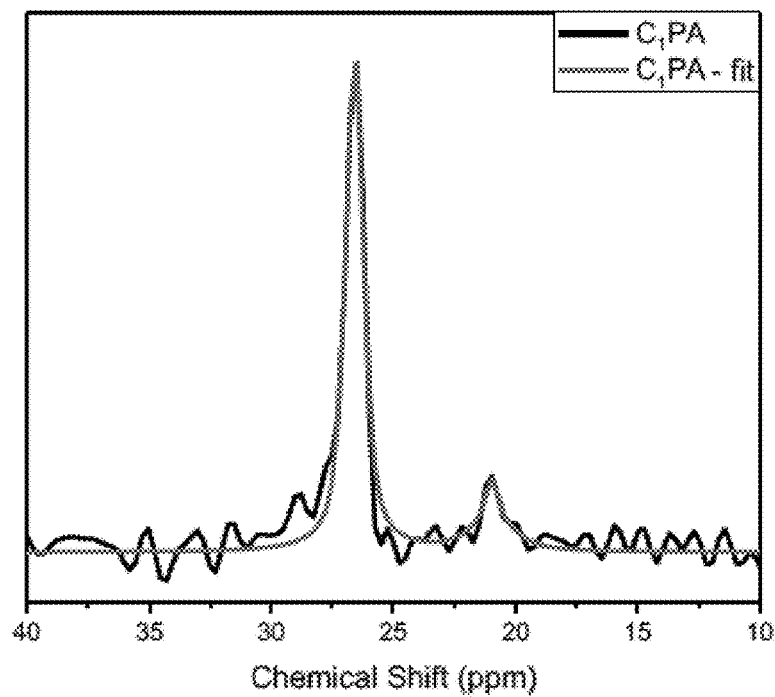
FIGS. 13A and 13B are plots of $P^{31}$ nuclear magnetic resonance (NMR) spectroscopy for $C_1$PA-modified zeolite 5A and $C_{18}$Pa-modified zeolite 5A, respectively.
Figure 13B:
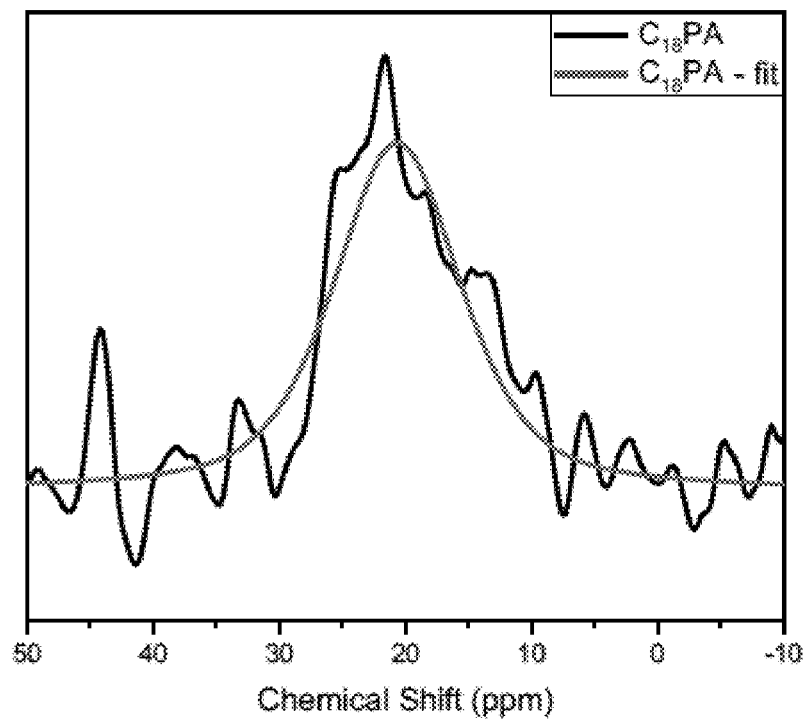

As illustrated by FIGS. 13A and 13B, phosphorus NMR shows that phosphorus exists in two distinct states in $C_1PA$-modified zeolite, but probably only one state in $C_{18}PA$-modified zeolite, suggesting that the binding mode or physical location of phosphorus in the two functionalized zeolites is different. Because the STEM and EDS data show a higher concentration of phosphorus near the surface of $C_1PA$-modified zeolite, and without wishing to be bound by any particular theory, the present inventors hypothesize that $C_1PA$ is more amenable to binding in positions that significantly constrain the pore openings near the surface of the zeolite particle, thus restricting gas diffusion but not altering the bulk structure of the zeolite. In this case, the "equilibrium" loading would not be significantly diminished; instead, the rates of adsorption of propane and n-butane are so slow that uptake cannot be measured over time scales relevant to industrial separation processes.

Examples 1-5 above demonstrate that the inventors have been able to select phosphonic acid modifiers to selectively tune diffusion and loadings of small molecules in zeolites. Adding $C_1PA$ to zeolites can increase the ideal adsorption selectivities in ethane/propane, ethane/n-butane, and propylene/propane separations by factors of 40 to 80; particularly, the propylene/propane ideal adsorption selectivity of 59 is of great interest and value given the difficulty and significant energy requirements of conventional propylene/propane separations. Without wishing to be bound by any particular theory, $C_1PA$ appears to partially penetrate into a zeolite during deposition of the monolayer, so as to dramatically change adsorption and diffusion characteristics of some molecules without affecting the zeolite's bulk crystalline structure.

Example 6

Phosphonic Acid Monolayer Formation on SAPO-34 Zeolite

SAPO-34 zeolite powders were synthesized by both microwave and non-microwave synthesis, using a reactant mixture of 1.0 part aluminum oxide, 2.0 parts phosphorus pentoxide ($P_2O_5$), 0.6 part silicon dioxide, 4.0 parts tetraethylammonium hydroxide (($C_2H_5)_4N(OH)$, "TEAOH"), and 75 parts water ($H_2O$). 200 mg of powder was mixed with a volume of a 10 mM phosphonic acid-in-toluene solution (stirred for 2 to 3 hours prior to addition of powder to facilitate dissolution) sufficient to provide a 10-fold stoichiometric excess of the phosphonic acid monomer. This mixture was vigorously stirred overnight (600 to 700 rpm for 16 to 24 hours), centrifuged (7000 rpm for 5 minutes), and decanted, and the resulting powder was then annealed in an oven at 120° C. for 4.5 hours. On the day after annealing, the annealed, functionalized zeolite powder was broken with a spatula and then rinsed (by adding liquid, mixing with vigorous shaking and 10 seconds in a vortex mixer, centrifuging, and decanting) three times with toluene and once with THF. As used in this and all subsequent materials, unless otherwise noted, the term "native material" refers to SAPO-34 that has been subjected to the process described in this paragraph, except that the liquid to which the calcine was added was pure toluene (i.e. did not contain phosphonic acid).

Figure 14:
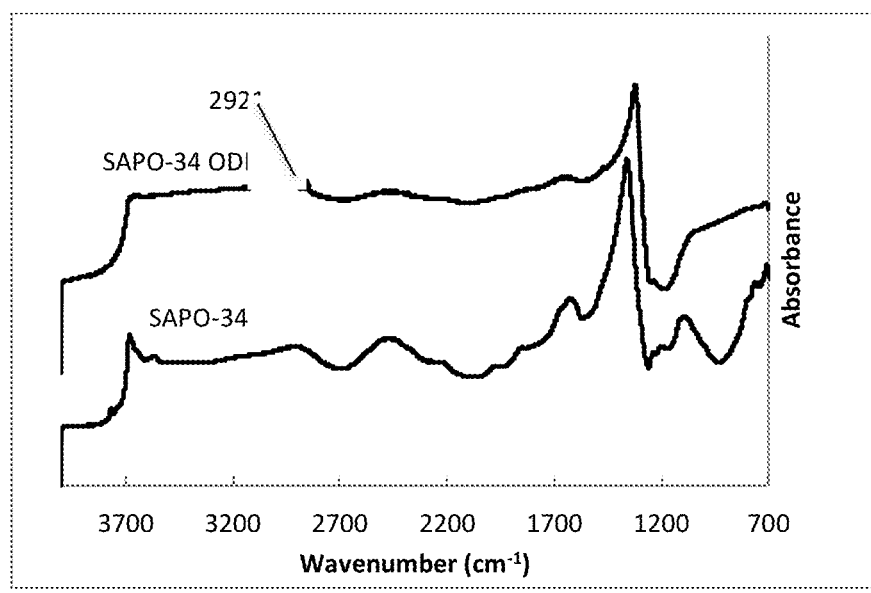
FIG. 14 is a plot of infrared (IR) spectra of SAPO-34 powder before treatment and after treatment with 5 mM $C_{18}$PA in toluene and 4.5 hours of annealing.

As illustrated by FIG. 14, the presence of a phosphonic acid monolayer on the surface of SAPO-34 treated with $C_{18}PA$ can be confirmed by IR spectroscopy. The $C_{18}PA$ monomer presents an IR peak corresponding to the asymmetric vibrations between hydrocarbon tails at 2921±4 cm$^{-1}$ when arranged in a monolayer. Lower wavenumbers indicate a more densely packed monolayer having a more ordered crystalline structure, and a further decrease in wavenumber below 2917 cm$^{-1}$ suggests the presence of pure $C_{18}PA$, which has an even more ordered crystalline structure.

Referring again to the IR spectra of FIG. 14, the $C_{18}PA$-modified zeolite shows the characteristic $C_{18}PA$ peaks at 2851 and 2921 cm$^{-1}$, which are absent in the untreated sample. The peak corresponding to the asymmetric hydrocarbon vibration is located at 2921 cm$^{-1}$, indicating a fairly ordered monolayer without pure $C_{18}PA$.

The mass that the monolayer contributes to the functionalized zeolite was measured by thermogravimetric analysis (TGA) and compared to the calculated mass of a complete monolayer to determine if physisorbed layers or other impurities may be present. Microwave-synthesized SAPO-34 particles have a cubic structure and an average width (a) of 300 nm; thus, the particles have a volume $a^3$ of $2.7 \cdot 10^7$ nm$^3$ and a surface area $6a^2$ of $5.4 \cdot 10^5$ nm$^2$. The framework density of SAPO-34, equal to the density of silicon and aluminum atoms, is 15.1 atoms per cubic nanometer, and from this it can be calculated that the density of the zeolite is $4.06 \cdot 10^{21}$ g/nm$^3$; multiplying this by the volume gives an approximate mass of one zeolite particle of $1.10 \cdot 10^{-13}$ g. To calculate the mass of the monolayer, the packing density was estimated. $C_{18}PA$ molecules bind to hydroxyl groups on the surface of the zeolite particle, but little is known about the density of the hydroxyl groups or how zeolite bonds terminate at the surface of the particle. To get an estimate of maximum coverage, the monomers were approximated as perfectly packed squares with a width equal to the kinetic diameter of the phosphonic acid molecule, which (because the alkyl tail is the widest part of the molecule) is approximated as equal to the diameter of the alkyl tail, in this case 0.43 nm. Dividing the calculated surface area of the zeolite particle ($5.4 \cdot 10^5$ nm$^2$) by this value gives an approximation of the number of monomer molecules per particle as $2.92 \cdot 10^6$; multiplying by the molecular weight of $C_{18}PA$ gives a total mass of $C_{18}PA$ per zeolite particle of $1.62 \cdot 10^{-15}$ g, or 1.5% of the mass of the functionalized zeolite. TGA, however, measured the monolayer as making up 5% of the particle mass; this deviation from the calculated value, combined with the IR results illustrated by FIG. 14, suggest that $C_{18}PA$, has been deposited on the zeolite surface with few impurities or multilayers.

Example 7

Effect of Phosphonic Acid Monolayer on Gas Adsorption of SAPO-34 Zeolite

Samples of the functionalized zeolite described in Example 6 were loaded into a bulbous sample cell by funneling the powder into the cell using weigh paper and then forcing the sample into the spherical part of the cell with a pipe cleaner. A glass rod was added to the sample cell, and the sample cell was attached to a Quantachrome Autosorb-1 device using the given fittings, with the O-ring lightly greased with vacuum grease; the Autosorb was operated in manual mode to evacuate the sample cell, first with the fine vacuum valve and then with the coarse vacuum valve after the pressure inside the cell dropped below 30 torr. Once the pressure in the cell dropped below 10 torr, a heating jacket was placed around the spherical portion of the cell, and the sample was outgassed at 200° C. overnight, after which the heating jacket was removed and the cell cooled to room temperature. The volume of the sample cell was then determined by filling the manifold of the sample cell with helium, allowing the helium to expand into the sample cell, and recording the pressure drop due to the expansion; the sample cell was then evacuated by coarse vacuum at room temperature for 20 minutes to remove any helium.

To test gas adsorption of the functionalized zeolite, the manifold was filled with the adsorbate gas to a pressure of 200 to 220 torr (for carbon dioxide or methane) or 1000 to 1040 torr (for propane or n-butane), monitored via the pressure display on the Autosorb device or a LabVIEW computer program. The initial adsorbate pressure in the manifold was recorded by LabVIEW, with the input still on the manifold pressure gauge. The pressure was then allowed to equilibrate (typically less than 1 minute for carbon dioxide or methane and about 10 minutes for propane or n-butane), and, with the LabVIEW program now monitoring the sample cell pressure gauge, the valve between the sample cell and the manifold was opened for just enough time to allow the two volumes to equilibrate in pressure and then immediately closed. The pressure over time in the sample cell was then recorded on the LabVIEW every 0.5 seconds, or every 5 seconds for samples with slower adsorption rates, until the pressure reached and maintained a constant value.

Samples were then outgassed for 1 hour, or longer if the pressure increased in the sample cell when the valve was closed after 1 hour, to remove adsorbed gases. The sample cell was then cooled to room temperature and removed from the Autosorb by filling to atmospheric pressure with helium. Once removed from the Autosorb, the cell was immediately weighed. Sample cell volume was calculated based on the ideal gas law and the manifold pressure reported by the Autosorb; the sample cell and manifold volumes were then used to calculate the change in adsorbate pressure from expansion based on the initial adsorbate pressure. The decrease in pressure beyond that expected from expansion was then converted to a molar quantity via the ideal gas law, where the volume is that of the sample cell (for propane or n-butane) or the combined volume of the manifold and sample cell (for carbon dioxide or methane). The sample mass was calculated as the net mass difference between the mass of the bulb and glass rod measured before testing and the mass of the outgassed sample, bulb, and glass rod measured after testing, from which the adsorption capacity on a mass basis (moles absorbed per gram) was calculated. The adsorption rate was quantified by the slope of the initial linear region (approximated as beginning when adsorption equals zero) of the adsorption-over-time curve; this regime often lasted minutes for treated samples, but unmodified samples adsorbed gases quickly and a rough estimate of slope could be gathered from the first few time points. Some adsorption testing was carried out at elevated temperature (although the helium testing was always done at room temperature to obtain accurate sample volume), although not all of a sample may have been at the elevated temperature because the heating jacket used did not cover the entire volume of the sample cell.

As illustrated by FIGS. 15A through 15D, $C_{18}PA$ monolayers slowed the adsorption of propane and n-butane into the pores of the SAPO-34 zeolite. The rates of propane and n-butane adsorption (FIGS. 15A and 15B), calculated by the slope of the initial linear region of the curves, were decreased by factors of 12 and 32, respectively, in the $C_{18}PA$-modified zeolite relative to the native material; by contrast, deposition of the $C_{18}PA$ monolayer had a smaller effect on the adsorption rate of methane (FIG. 15D), and no discernible effect on the adsorption rate of carbon dioxide (FIG. 15C).

The lack of effect on carbon dioxide adsorption rate is particularly important because high carbon dioxide permeability is critical for separating carbon dioxide from natural gas; carbon dioxide decreases the energy contact of natural gas and is corrosive to pipelines in the presence of water, and current amine adsorption processes for removing the carbon dioxide are economically and energetically inefficient. Methane diffusion is slowed, but to a lesser extent than the longer hydrocarbons. The weight of the functionalized zeolite was adjusted for the monolayer mass as determined by TGA so that adsorption values are based on weight of the zeolite alone. Total methane and propane adsorption capacities for the $C_{18}PA$-coated zeolite closely match that of the untreated zeolite, but n-butane and carbon dioxide adsorption capacities are 13-16% lower.

N-butane was also adsorbed on SAPO-34 powder that was exposed to toluene. As illustrated by FIG. 16, toluene exposure of the zeolite did not appear to affect adsorption; without wishing to be bound by any particular theory, this suggests that the decreased rate of n-butane adsorption in treated powders is due to the monolayer, not the solvent.

Figure 17:
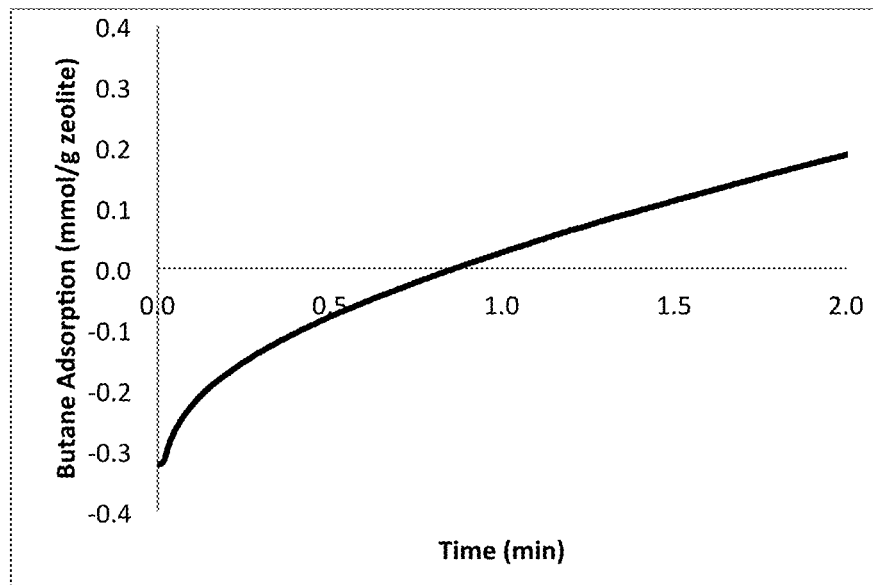
FIG. 17 is a plot of n-butane adsorption on SAPO-34 powder, treated with 5 mM $C_{18}$PA in toluene and annealed for 4.5 hours, as a function of time.
Figure 18:
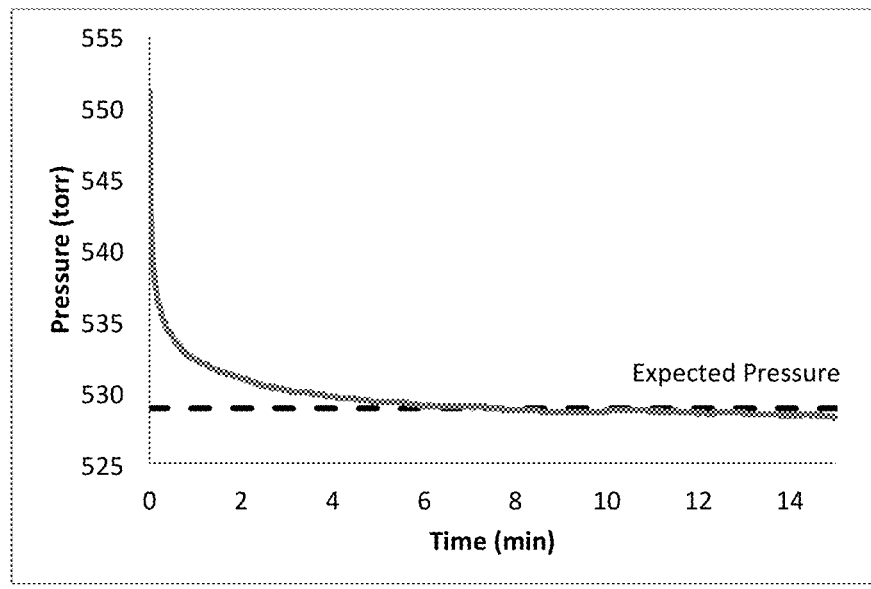
FIG. 18 is a plot of a change in n-butane pressure over time in an empty sample cell after expansion.

As previously discussed, gas adsorption rates were estimated from the initial slope of adsorption over time, but this curve is not, or at least not in all cases, linear over the initial time range. FIG. 17 illustrates n-butane adsorption on a $C_{18}PA$-modified sample over the first two minutes of adsorption; the adsorption values are initially negative and evince a logarithmic curve. An n-butane adsorption test run on an empty sample cell resulted in the same effect, as illustrated by FIG. 18. The initially negative adsorption values show that the n-butane pressure is higher than predicted by the ideal gas law, which, without wishing to be bound by any particular theory, may indicate that the n-butane diffuses into the sample cell slowly. The same phenomenon is not observed in tests of untreated and/or native zeolites, possibly because the untreated zeolite adsorbs n-butane so quickly that the initial pressure increase does not occur; while this may introduce error into the calculated rate values, overall results are not significantly affected because differences in alkane adsorption rates between modified and unmodified zeolites are roughly six times greater than the difference between slopes calculated from different time ranges on the same sample.

Example 8

Effect of Anneal Duration on Gas Adsorption

Zeolite samples were prepared according to the procedure described in Example 6, except that some samples were subjected to a different anneal time to investigate the effect of this parameter on gas adsorption.

Figure 19:
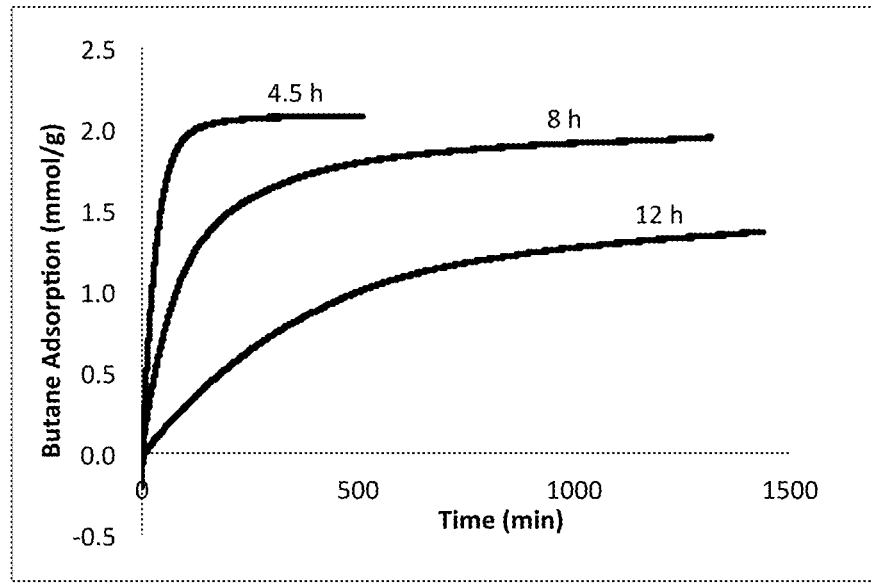
FIG. 19 is a plot of n-butane adsorption on SAPO-34, annealed for various durations, as a function of time.

N-butane was adsorbed onto $C_{18}PA$-functionalized samples annealed for 4.5 hours, 8 hours, and 12 hours. As illustrated by FIG. 19, longer anneal times correlated with lower adsorption rates. The total adsorption of n-butane by these zeolite samples, determined by TGA, and the decrease thereof relative to the native material, is presented in Table 4.

TABLE 4

Decrease in butane adsorption as a result of varied anneal times

| Anneal time (hr) | Monomer mass fraction (%) | Decrease in n-butane adsorption (%) |
|---|---|---|
| 4.5 | 5.2 | 3.7 |
| 8 | 13.8 | 10.2 |
| 8 | 13.3 | 11.1 |
| 12 | 25.4 | 37.0 |

Figure 20:
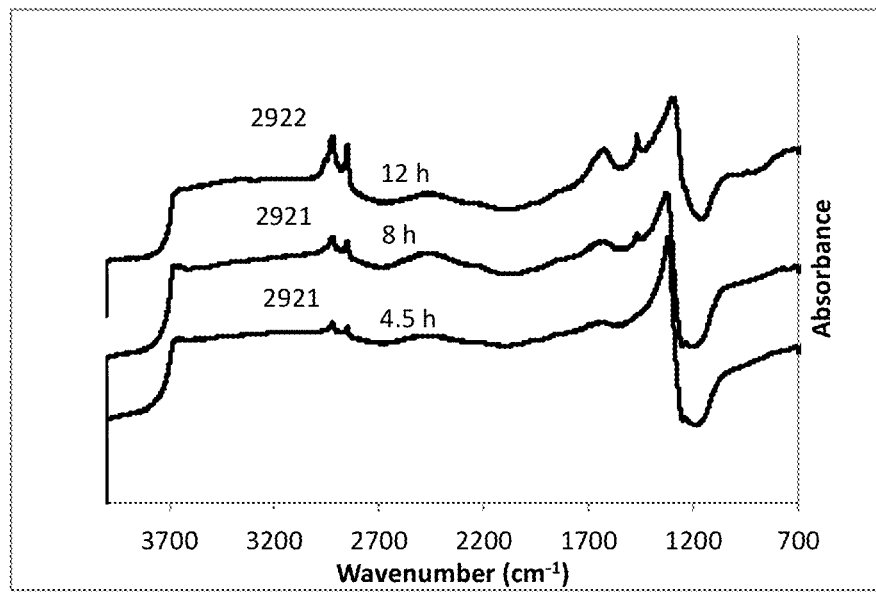
FIG. 20 is a plot of IR spectra for SAPO-34, treated with 5 mM $C_{18}$PA in toluene and annealed for various durations.

As shown in Table 4, and without wishing to be bound by any particular theory, longer anneal times may result in more organized and dense packing of both the monolayer and any physisorbed multilayers. More densely packed multilayers interact more strongly with the monolayer to which they are physisorbed, and increasing anneal time may therefore create multilayers that are too strongly physisorbed to be effectively washed off by toluene or THF, resulting in multilayers on the final sample. The formation of such multilayers would cause a greater increase in weight and, potentially, a further decrease in n-butane adsorption rate, due to the presence of more material at the surface. IR spectra of these samples are illustrated by FIG. 20.

Example 9

Effect of Phosphonic Acid Concentration on Gas Adsorption

Zeolite samples were prepared according to the procedure described in Example 6, except that some samples were subjected to a different concentration of phosphonic acid in the toluene solution to investigate the effect of this parameter on gas adsorption.

Figure 21:
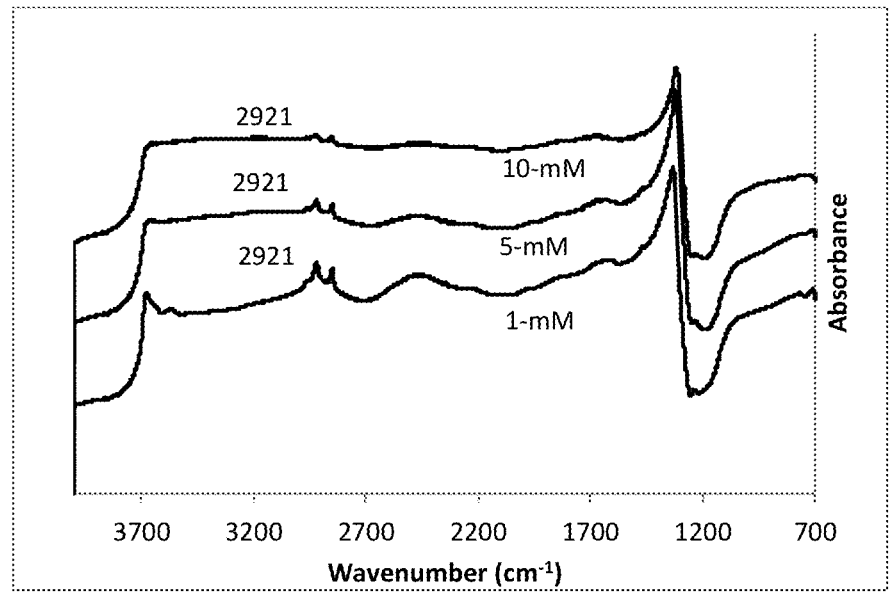
FIG. 21 is a plot of IR spectra for SAPO-34, treated with $C_{18}$PA of various concentrations in toluene and annealed for 4.5 hours.
Figure 22:
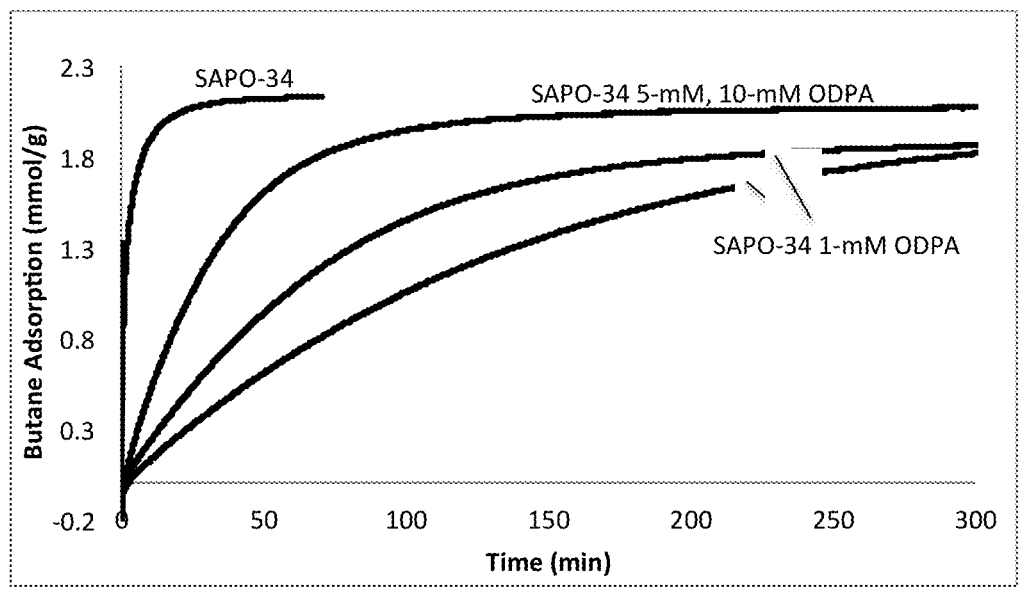
FIG. 22 is a plot of n-butane adsorption on SAPO-34, with $C_{18}$PA layers deposited in toluene solutions of various concentrations and 4.5 hours of annealing, as a function of time.

N-butane was adsorbed onto native material and onto zeolite samples functionalized in 1 mM, 5 mM, and 10 mM $C_{10}PA$ solutions. As illustrated by FIG. 21, 10 mM and 5 mM solutions result in roughly the same effect on adsorption (i.e. decreased relative to native material), but adsorption rates are further decreased by a 1 mM solution. These results are contrary to what would be expected by decreasing concentration; the monolayer would be expected to pack less densely for a lower monomer concentration and thus result in a smaller decrease in n-butane adsorption rate. IR spectra of these samples are illustrated by FIG. 22.

Example 10

Effect of Phosphonic Acid Alkyl Tail Length on Gas Adsorption

Figures 23A, 23B:
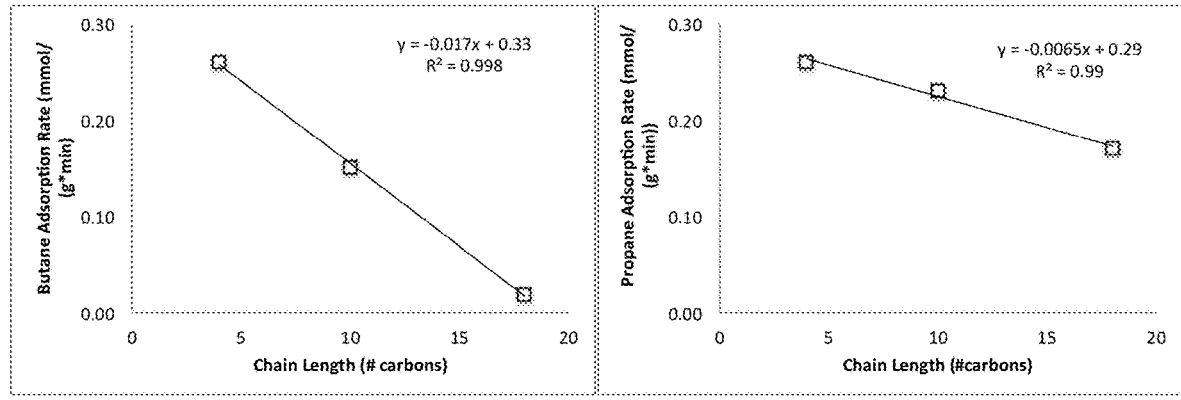
FIGS. 23A and 23B are plots of the adsorption rate of n-butane and propane, respectively, on non-microwave-synthesized SAPO-34 modified in a 10 mM phosphonic acid solution with tetrahydrofuran (THF), as a function of phosphonic acid alkyl tail length.

Zeolite samples were prepared according to the procedure described in Example 6, except that the solvent was THF rather than toluene, using three different phosphonic acids—$C_4PA$, $C_{10}PA$, and $C_{18}PA$—to investigate the effect of alkyl tail length on gas adsorption. As illustrated by FIGS. 23A and 23B, propane and n-butane adsorption rates decreased with increasing alkyl tail length, with n-butane adsorption being more strongly affected than propane adsorption.

Figure 24:
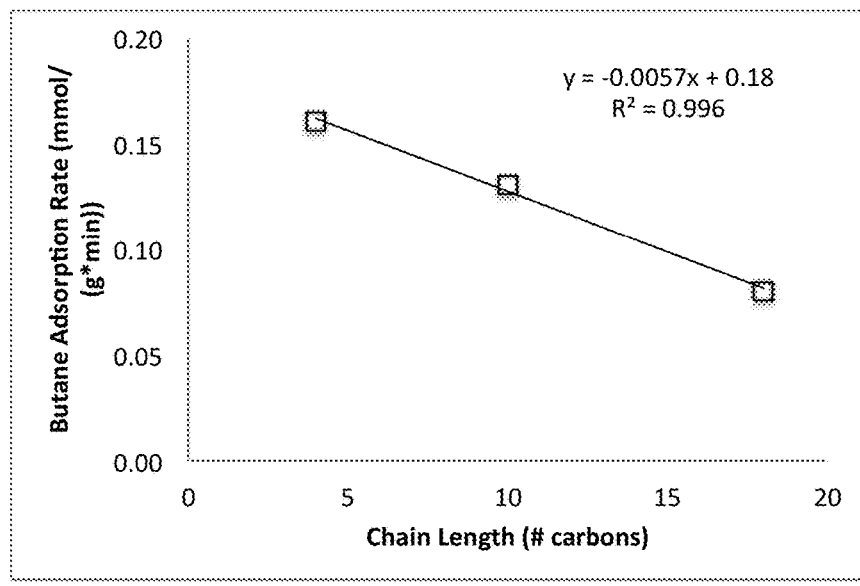
FIG. 24 is a plot of n-butane adsorption rate on microwave-synthesized SAPO-34 modified in a 5 mM phosphonic acid solution with toluene and annealed for 4.5 hours, as a function of phosphonic acid alkyl tail length.
Figure 25:
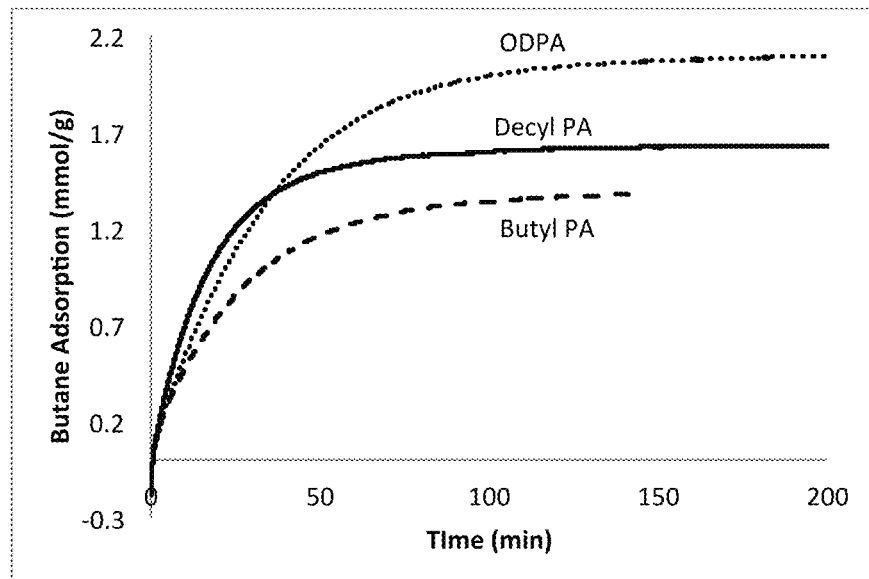
FIG. 25 is a plot of n-butane adsorption rate on microwave-synthesized SAPO-34 modified in a 5 mM phosphonic acid solution in toluene and annealed for 4.5 hours for various phosphonic acids.

Subsequent to this test, the present inventors discovered that use of THF as a solvent rather than toluene tends to decrease total adsorption (see Example 12 below); while all samples whose test results are illustrated by FIGS. 23A and 23B were prepared in the same solvent (and therefore the trend in adsorption should be due to change in alkyl tail length rather than the monomer), the same test was replicated using toluene as the solvent. As illustrated by FIG. 24, a linear trend between n-butane uptake and alkyl tail length was observed, but the effect is not as pronounced as for the samples prepared in THF. Additionally, as illustrated by FIG. 25, the total amount of n-butane adsorbed decreased with decreasing alkyl tail length. Monolayers of longer alkyl tails were expected to decrease adsorption capacity to a greater extent because such layers should cause a greater increase in the weight of the particles; thus, it is possible that the shorter phosphonic acids used contained impurities or formed multilayers, given that the solution concentrations and anneal times used were optimized for $C_{18}PA$ rather than other phosphonic acids.

Example 11

Figure 26A:
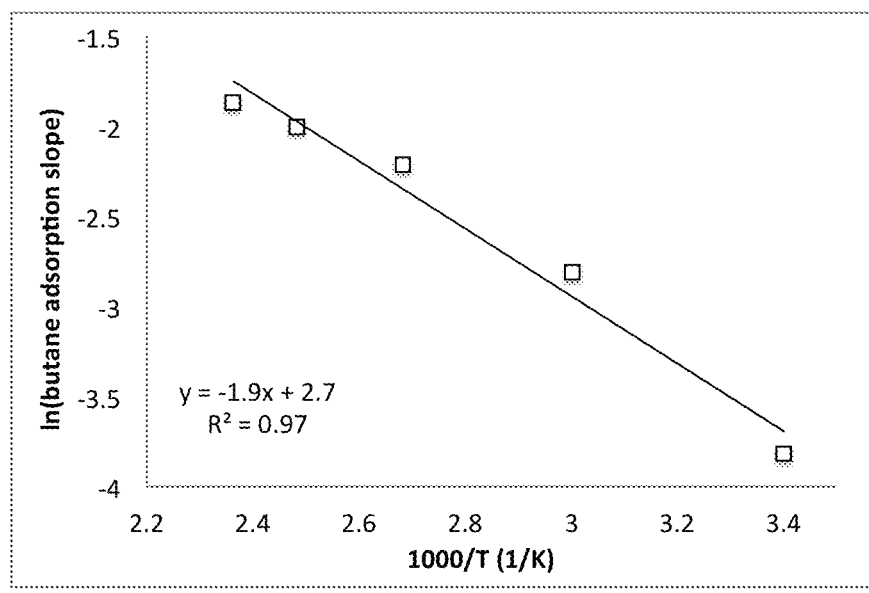
FIGS. 26A and 26B are plots of the natural logarithm of n-butane adsorption slope as a function of the inverse of temperature, fit with one and two trendlines, respectively.
Figure 27:
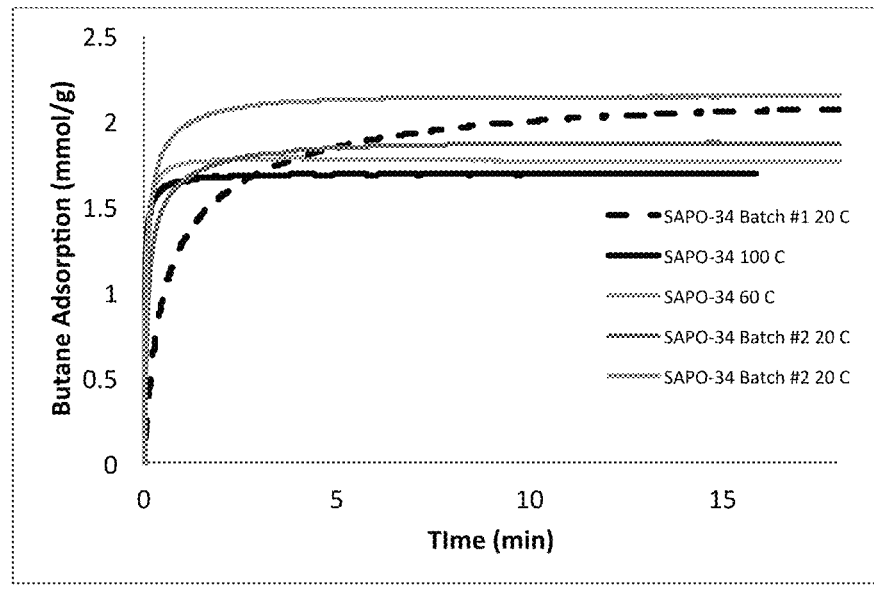
FIG. 27 is a plot of n-butane adsorption on unmodified SAPO-34 at various temperatures, as a function of time.
Figure 28A:
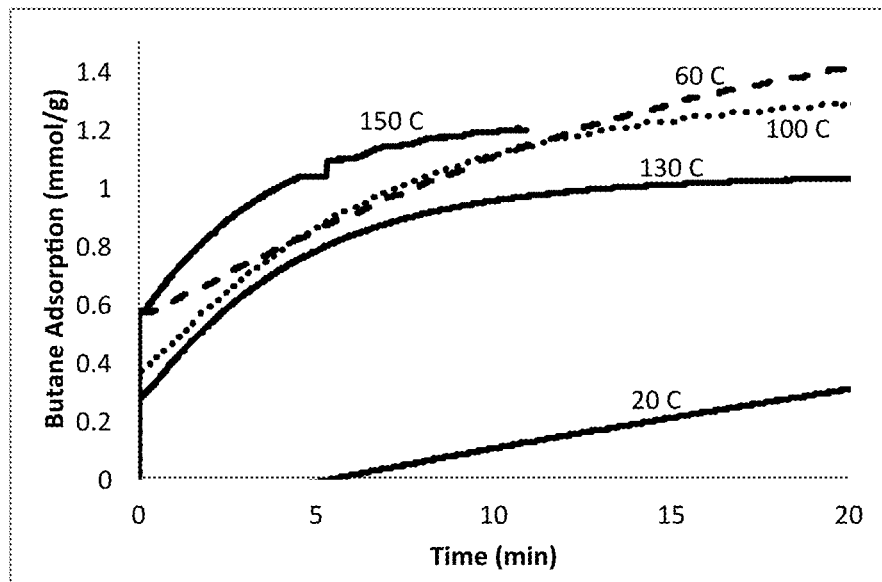
FIGS. 28A and 28B are plots of n-butane adsorption, respectively with and without adjustment for initial increase in adsorption, on SAPO-34 modified with 10 mM $C_{18}$PA in toluene at various temperatures, as a function of time.
Figure 28B:
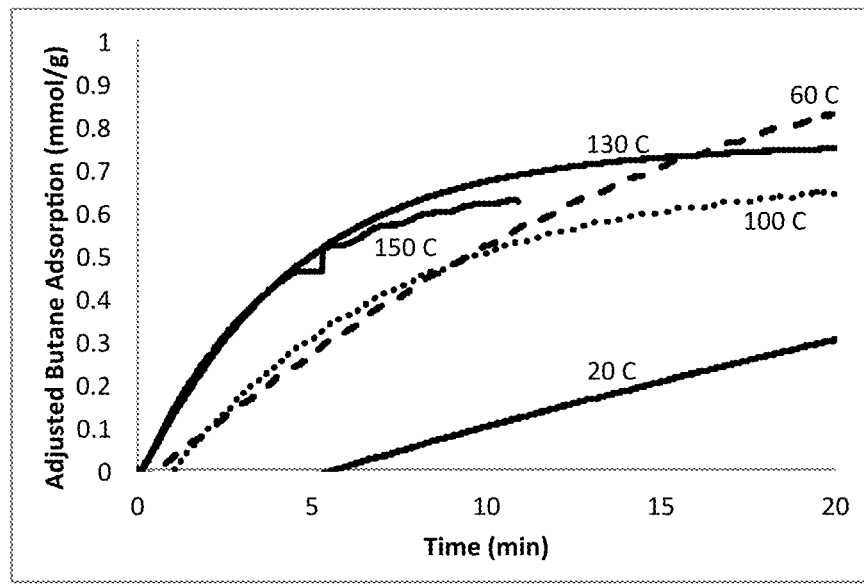

Effect of Adsorption Temperature on Gas Adsorption $C_{18}PA$-modified zeolite samples were prepared according to the procedure described in Example 6, and n-butane was adsorbed onto these samples and native material at a series of temperatures, as illustrated by FIG. 26A. The slope of the trendline corresponds to an activation energy of 16±5 kJ/mol for n-butane diffusion through the monolayer and adsorption in the pores. The adsorption rate in native material did not change with temperature, indicating that the main barrier to adsorption is the monolayer coating. The n-butane adsorptions over time at various temperatures for both the $C_{18}PA$-modified zeolite and the native material are illustrated in FIGS. 27, 28A, and 28B and presented numerically in Table 5.

TABLE 5

N-butane adsorption at various temperatures

| Temperature (° C.) | Adjusted n-butane adsorption (mmol/g) | Unadjusted n-butane adsorption (mmol/g) |
|---|---|---|
| 20 | — | 1.24 |
| 60 | 1.15 | 1.73 |
| 100 | 0.72 | 1.38 |
| 130 | 0.8 | 1.08 |
| 150 | 0.62 | 1.19 |

Figure 26B:
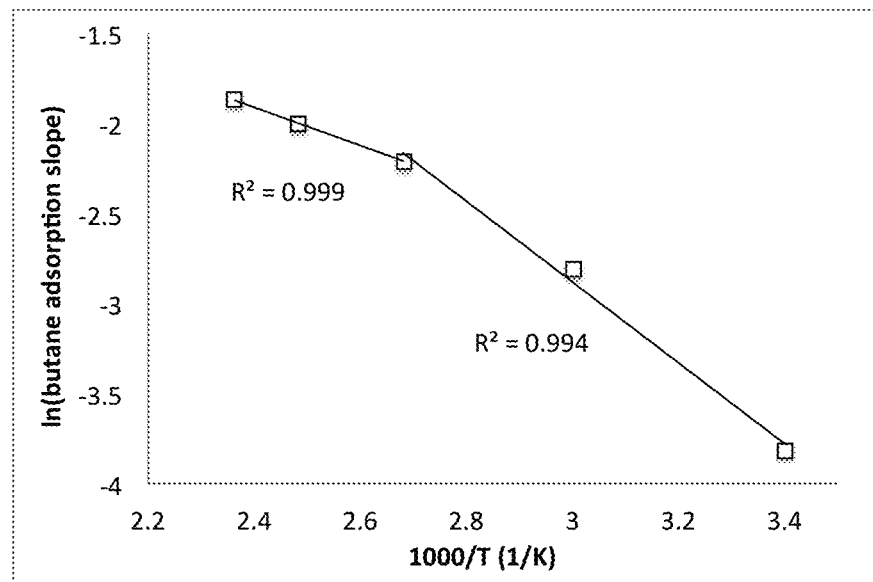

The data more closely fit a model with two trendlines, where the slope changes at approximately 100° C. (373 K), as illustrated by FIG. 26B. Tests on zirconium dioxide substrates have shown that $C_{18}PA$ monolayers are in a solid-like state at room temperature, such that the alkyl tails are rigid and immobile, but have been shown to transition to a liquid-like state, in which the head group is still bound to the surface of the particle but the alkyl tails may move more freely, at temperatures above about 50° C. (323 K); thus, without wishing to be bound by any particular theory, the change in slope could indicate that the monolayer undergoes a similar transition, but at a higher temperature, on zeolite substrates.

Example 12

Examination of Interaction Between Tetrahydrofuran Solvent and Zeolites

Some zeolite samples were prepared according to the procedure described in Example 6, except that THF rather than toluene was used as the solvent. These samples were generally characterized by decreased gas adsorption relative to samples functionalized in toluene solutions; as illustrated by FIG. 29, n-butane adsorption tests reveal that the change in solution is responsible for this decrease.

Without wishing to be bound by any particular theory, one possible explanation for this phenomenon is that the specific zeolite used in this Example (SAPO-34) is known to be a catalyst for dimethyl ether conversion, a reaction that is typically carried out at temperatures of about 500° C. (773 K) but that may, due to the presence of the THF ether bond, occur at low levels at the temperatures involved in this test, particularly during annealing at 120° C. (393 K). Comparison of n-butane adsorption on $C_{18}PA$-modified zeolite to n-butane adsorption on native material exposed only to THF reveals that THF slows adsorption by a factor of 36, but the addition of the $C_{18}PA$ monolayer slows the uptake rate by a factor of 210.

Example 13

Effect of $C_{18}PA$ Coating on Water Adsorption

Zeolites functionalized with $C_{18}PA$ according to the procedure of Example 6 were exposed to water; the contact angles resulting from this exposure are illustrated by FIGS. 30A through 30C. The contact angle results indicate that the modified material is hydrophobic, whereas the native material is hydrophilic. Water vapor adsorption kinetics and capacity were measured on these samples and revealed no differences relative to the native material, as illustrated by FIG. 31; thus, functionalization with $C_{18}PA$ affects contact angle but not adsorption characteristics, and the contact angle does not correlate with the native material's interaction with vapor-phase water.

Examples 6-13 indicate that surface modification with a phosphonic acid monolayer decreases the rate of adsorption of propane and n-butane into zeolites, has a small effect on methane adsorption, and has little or no effect on adsorption of carbon dioxide or water. Without wishing to be bound by any particular theory, these results suggest that alkane molecules may have an affinity for the monolayer due to van der Waals forces, causing the alkanes to spend more time in the monolayer before entering the pores of the zeolite. These results are consistent with previous studies that demonstrated the affinity between alkanes and hydrocarbon monolayers.

The van der Waals effect would be greater for longer hydrocarbon adsorbates, as each additional carbon atom contributes more potential for van der Waals interactions. This is consistent with the stronger effect seen on longer hydrocarbons. The same principle applies to increasing the alkyl tail length of the monolayer; as the alkyl tail length increases, so too does the number of sites for van der Waals interaction that the adsorbate passes through before reaching the pore opening. Thus, the alkane would take more time to pass through a longer-tailed monolayer, which is consistent with results from testing coatings of monomers of different tail lengths. However, longer tails can also create a more densely packed monolayer; since van der Waals attraction between the monomer tails is the driving force for monolayer packing, self-assembly is greater for longer chains.

Although the mechanism of van der Waals forces is consistent with the results, other possibilities exist. The diameter of SAPO-34 pores, as used in Examples 6-13, is barely wide enough to fit molecules of linear alkanes having three or more carbon atoms. Adding a monolayer may crowd the surface enough to make it harder for these longer molecules to fit through the pore openings, slowing adsorption.

The invention illustratively disclosed herein suitably may be practiced in the absence of any element which is not specifically disclosed herein. It is apparent to those skilled in the art, however, that many changes, variations, modifications, other uses, and applications of the invention are possible, and also changes, variations, modifications, other uses, and applications which do not depart from the spirit and scope of the invention are deemed to be covered by the invention, which is limited only by the claims which follow.

The foregoing discussion of the invention has been presented for purposes of illustration and description. The foregoing is not intended to limit the invention to the form or forms disclosed herein. In the foregoing Detailed Description of the Invention, for example, various features of the invention are grouped together in one or more embodiments for the purpose of streamlining the disclosure. The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of the Invention, with each claim standing on its own as a separate preferred embodiment of the invention.

Moreover, though the description of the invention has included description of one or more embodiments and certain variations and modifications, other variations, combinations, and modifications are within the scope of the invention, e.g. as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

The invention claimed is:

1. A functionalized zeolite, comprising:
   a zeolite substrate comprising zeolite 5A; and
   a self-assembled monolayer of methylphosphonic acid, disposed on a surface of the zeolite substrate.

2. The functionalized zeolite of claim 1, wherein the zeolite substrate is annealed.

3. The functionalized zeolite of claim 1, wherein the zeolite substrate comprises at least one of a powder and a pellet.

4. The functionalized zeolite of claim 1, wherein the zeolite substrate further comprises at least one zeolite selected from the group consisting of SAPO-34 zeolite, MFI zeolites, chabazite zeolites, Y zeolite, faujasite zeolites, ferrierite zeolites, mordenite zeolites, SSZ-13 zeolite, and ZSM-5 zeolite.

5. The functionalized zeolite of claim 1, wherein at least a portion of the self-assembled monolayer is disposed on or within a pore of the zeolite substrate.

6. The functionalized zeolite of claim 1, wherein at least one of the following is true:
   (i) the functionalized zeolite has a propylene/propane ideal adsorption selectivity of at least about 45;
   (ii) the functionalized zeolite has an ethane/propane ideal adsorption selectivity of at least about 44; and
   (iii) the functionalized zeolite has an ethane/n-butane ideal adsorption selectivity of at least about 13.

* * * * *